United States Patent
Qiu et al.

(10) Patent No.: US 10,189,846 B2
(45) Date of Patent: Jan. 29, 2019

(54) HEPATITIS B ANTIVIRAL AGENTS

(71) Applicant: ENANTA PHARMACEUTICALS, INC., Watertown, MA (US)

(72) Inventors: Yao-Ling Qiu, Andover, MA (US); Hui Cao, Belmont, MA (US); Xiaowen Peng, Sudbury, MA (US); Wei Li, Lexington, MA (US); Jorden Kass, Belmont, MA (US); Xuri Gao, Newton, MA (US); Meizhong Jin, Wellesley, MA (US); Yat Sun Or, Watertown, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 15/617,445

(22) Filed: Jun. 8, 2017

(65) Prior Publication Data
US 2017/0355701 A1 Dec. 14, 2017

Related U.S. Application Data

(60) Provisional application No. 62/443,245, filed on Jan. 6, 2017, provisional application No. 62/348,419, filed on Jun. 10, 2016.

(51) Int. Cl.
*A61K 31/519* (2006.01)
*C07D 487/04* (2006.01)
*A61P 31/20* (2006.01)
*A61K 45/06* (2006.01)

(52) U.S. Cl.
CPC .......... *C07D 487/04* (2013.01); *A61K 31/519* (2013.01); *A61P 31/20* (2018.01); *A61K 45/06* (2013.01)

(58) Field of Classification Search
CPC .......................... A61K 31/519; C07D 487/04
USPC ........................................ 514/259.1; 544/282
See application file for complete search history.

(56) References Cited

U.S. PATENT DOCUMENTS

| 3,385,756 | A | 5/1968 | Chupp et al. |
| 3,975,532 | A | 8/1976 | Miller |
| 4,285,946 | A | 8/1981 | Kampe et al. |
| 4,507,481 | A | 3/1985 | Davidson et al. |
| 5,510,387 | A | 4/1996 | Leonidov et al. |
| 5,656,644 | A | 8/1997 | Adams et al. |
| 6,498,165 | B1 | 12/2002 | Armstrong et al. |
| 6,503,913 | B1 | 1/2003 | Goldmann et al. |
| 6,667,342 | B1 | 12/2003 | Clarke et al. |
| 7,232,825 | B2 | 6/2007 | Chen et al. |
| 7,411,003 | B1 | 8/2008 | Liu et al. |
| 7,741,494 | B2 | 6/2010 | Bressi et al. |
| 8,202,876 | B2 | 6/2012 | Albaugh et al. |
| 8,420,823 | B2 | 4/2013 | Sato et al. |
| 9,447,086 | B2 | 9/2016 | Guo et al. |
| 9,498,479 | B2 | 11/2016 | Zhang et al. |
| 9,573,941 | B2 | 2/2017 | Ren et al. |
| 9,617,252 | B2 | 4/2017 | Liu et al. |
| 2003/0232842 | A1 | 12/2003 | Goldmann et al. |
| 2005/0203119 | A1 | 9/2005 | Ono et al. |
| 2007/0219239 | A1 | 9/2007 | Mjalli et al. |
| 2007/0225373 | A1 | 9/2007 | Chen et al. |
| 2009/0023740 | A1 | 1/2009 | Fulp et al. |
| 2011/0009622 | A1 | 1/2011 | Jitsuoka et al. |
| 2011/0165118 | A1 | 7/2011 | Chan et al. |
| 2011/0281950 | A1 | 11/2011 | Baiocchi et al. |
| 2012/0009142 | A1 | 1/2012 | Karp et al. |
| 2013/0251673 | A1 | 9/2013 | Hartman et al. |
| 2013/0267517 | A1 | 10/2013 | Guo et al. |
| 2014/0343032 | A1 | 11/2014 | Guo et al. |
| 2015/0005295 | A1 | 1/2015 | Vandyck et al. |
| 2015/0119362 | A1 | 4/2015 | Gurney et al. |

(Continued)

FOREIGN PATENT DOCUMENTS

CN 106810548 A 6/2017
CN 106928215 A 7/2017

(Continued)

OTHER PUBLICATIONS

Chemical Abstract Service STN Database Registry No. 1578268-77-5 [online][Entered STN: Apr. 1, 2014].
PubChem-CID, 63186259, Create Date: Oct. 22, 2012, p. 3.
PubChem, '610', Create Date: Jun. 14, 2012, Date Accessed: Jun. 17, 2016, p. 3, compound.
PubChem, '428', Create Date: Sep. 11, 2005, Date Accessed: Jun. 17, 2016, p. 3, compound.
PubChem-CID 23201920, Create Date: Dec. 5, 2007, p. 3.
Yang, et al., "Enzyme-mediated hydrolytic activation of prodrugs," Acta Pharmaceutica Sinica B., 1(3):143-159. 2011.

(Continued)

*Primary Examiner* — Jeffrey H Murray
(74) *Attorney, Agent, or Firm* — Edgar W. Harlan; Carolyn S. Elmore, Esq.; Elmore Patent Law Group, P.C.

(57) ABSTRACT

The present invention discloses compounds of Formula (I), or pharmaceutically acceptable salts, thereof:

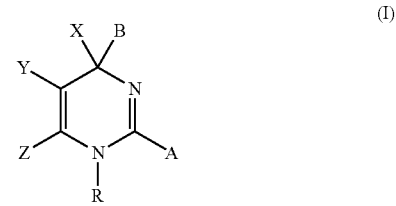

(I)

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

8 Claims, No Drawings

(56) References Cited

U.S. PATENT DOCUMENTS

| | | |
|---|---|---|
| 2015/0152096 A1 | 6/2015 | Zhang et al. |
| 2015/0197493 A1 | 7/2015 | Hartman |
| 2015/0252057 A1 | 9/2015 | Guo et al. |
| 2015/0274653 A1 | 10/2015 | Vandyck et al. |
| 2016/0206616 A1 | 7/2016 | Zhang et al. |
| 2016/0237078 A9 | 8/2016 | Guo et al. |
| 2016/0264562 A1 | 9/2016 | Liu et al. |
| 2016/0264563 A1 | 9/2016 | Verschueren et al. |
| 2016/0289212 A1 | 10/2016 | Qiu et al. |
| 2016/0332996 A1 | 11/2016 | Qiu et al. |
| 2016/0347746 A1 | 12/2016 | Zhang et al. |
| 2017/0014408 A1 | 1/2017 | Qiu et al. |
| 2017/0022150 A1 | 1/2017 | Qiu et al. |
| 2017/0217974 A1 | 8/2017 | Or et al. |
| 2017/0253609 A1 | 9/2017 | Qiu et al. |

FOREIGN PATENT DOCUMENTS

| | | |
|---|---|---|
| CN | 106928245 A | 7/2017 |
| WO | 0168641 A1 | 9/2001 |
| WO | 0168647 A1 | 9/2001 |
| WO | 2006033995 A2 | 3/2006 |
| WO | 2013006394 A1 | 1/2013 |
| WO | 2013096744 A1 | 6/2013 |
| WO | 2013130703 A2 | 9/2013 |
| WO | 20130130703 A2 | 9/2013 |
| WO | 2013144129 A1 | 10/2013 |
| WO | 2013181584 A2 | 12/2013 |
| WO | 2014184350 A1 | 11/2014 |
| WO | 2014184365 A1 | 11/2014 |
| WO | 2015/074546 A1 | 5/2015 |
| WO | 2015113990 A1 | 8/2015 |
| WO | 2015173164 A1 | 11/2015 |
| WO | 2015/180631 A1 | 12/2015 |
| WO | 2016071215 A1 | 5/2016 |
| WO | 2016128335 A1 | 8/2016 |
| WO | 2017013046 A1 | 1/2017 |
| WO | 2017017042 A1 | 2/2017 |
| WO | 2017017043 A1 | 2/2017 |
| WO | 2017140821 A1 | 8/2017 |
| WO | 2017205115 A1 | 11/2017 |
| WO | 2017216685 A1 | 12/2017 |
| WO | 2017216686 A1 | 12/2017 |
| WO | 2018019297 A1 | 2/2018 |
| WO | 2018022282 A1 | 2/2018 |
| WO | 2018047109 A1 | 3/2018 |
| WO | 2018073753 A1 | 4/2018 |
| WO | 2018085619 A1 | 5/2018 |

OTHER PUBLICATIONS

PubChem CID 69095846 {National Center for Biotechnology Information. PubChem Compound Database; CID=69095846, https://pubchem.ncbi.nlm.nih.gov/compound/69095846 (accessed May 23, 2017), create date Nov. 30, 2012.

PubChem CID 57036978, National Center for Biotechnology Information. PubChem Compound Database; CID=57036978, https://pubchem.ncbi.nlm.nih.gov/ compound/57036978 (accessed May 19, 2017), create date Jun. 13, 2012.

PubChem-SID 15224030, Deposit Date: Oct. 25, 2006, p. 3.

Chemical Abstracts Registry No. 1026741-09-2, indexed in the Registry file on Jun. 9, 2008.

PubChem CID 10194182, National Center for Biotechnology Information. PubChem Compound Database; CID=10194182, https://pubchem.ncbi.nlm.nih.gov/compound/10194182 (accessed May 19, 2017), create date Oct. 25, 2006.

Chemical Abstracts Registry No. 92555-24-3, indexed in the Registry file on Dec. 17, 1984.

Chemical Abstracts Registry No. 950067-32-0, indexed in the Registry file on Oct. 10, 2007.

HEPATITIS B ANTIVIRAL AGENTS

RELATED APPLICATIONS

This application claims the benefit of U.S. Provisional Application No. 62/348,419, filed on Jun. 10, 2016, and 62/443,245, filed on Jan. 6, 2017. The entire teachings of the above applications are incorporated herein by reference.

TECHNICAL FIELD

The present invention relates generally to novel antiviral agents. Specifically, the present invention relates to compounds which can inhibit the protein(s) encoded by hepatitis B virus (HBV) or interfere with the function of the HBV life cycle, compositions comprising such compounds, methods for inhibiting HBV viral replication, methods for treating or preventing HBV infection, and processes for making the compounds.

BACKGROUND OF THE INVENTION

HBV infection remains a major public health problem, affecting approximately 2 billion people worldwide. Among them, 350 million people worldwide and 1.4 million in the US develop a chronic infection, which can lead to chronic persistent hepatitis, liver cirrhosis, and hepatocellular carcinoma (HCC). Every year 500,000 to 1 million people die from the end stage of liver diseases caused by HBV infection.

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent HCC. Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid protein (CP) plays essential roles in HBV replication. The predominant biological function of capsid protein is to act as a structural protein to encapsidate pre-genomic RNA and form immature capsid particles, which spontaneously self-assemble from many copies of core dimers in the cytoplasm. Capsid protein also regulates viral DNA synthesis through different phosphorylation status of its C-terminal phosphorylation sites. Also, capsid protein might facilitate the nuclear translocation of viral relaxed circular genome by means of the nuclear localization signals located in the Arginine-rich domain of the C-terminal region of capsid protein. In the nucleus, as a component of viral cccDNA minichromosome, capsid protein could play a structural and regulatory role in the functionality of cccDNA minichromosomes. Capsid protein also interacts with viral large envelope protein in endoplasmic reticulum (ER) and triggers the release of intact viral particles from hepatocytes.

Capsid related anti-HBV inhibitors have been reported. For example, phenylpropen-amide derivatives, including compounds named AT-61 and AT-130 (Feld J. et al. Antiviral Res. 2007, 76, 168), and a class of thiazolidin-4-ones from Valeant (WO2006/033995), have been shown to inhibit pregenomic RNA (pgRNA) packaging. Heteroaryldihydropyrimi-dines or HAPs were discovered in a tissue culture-based screening (Weber et al., Antiviral Res. 2002, 54, 69). These HAP analogs act as synthetic allosteric activators and are able to induce aberrant capsid formation that leads to degradation of the core protein. A subclass of sulphamoyl-arylamides also shows activity against HBV (WO 2013/006394, WO 2013/096744, and WO 2014184365). It was also shown that the small molecule bis-ANS acts as a molecular 'wedge' and interferes with normal capsid-protein geometry and capsid formation (Zlotnick A. et al. J. Virol. 2002, 4848).

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds. Compounds of the present invention inhibit the protein(s) encoded by hepatitis B virus (HBV) or interfere with the life cycle of HBV and are also useful as antiviral agents. In addition, the present invention includes the process for the preparation of the said compounds.

In its principal aspect, the present invention provides a compound of Formula (I):

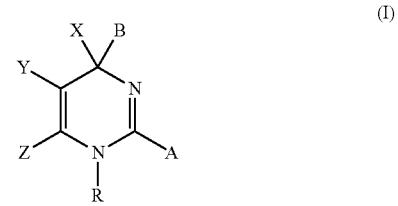

or a pharmaceutically acceptable salt thereof, wherein:

A is optionally substituted aryl or optionally substituted heteroaryl; preferably A is optionally substituted azolyl, optionally substituted pyridyl, or optionally substituted phenyl;

B is selected from the group consisting of hydrogen, halo, CN, optionally substituted —$C_1$-$C_6$ alkyl, and optionally substituted —$C_3$-$C_6$ cycloalkyl; preferably B is hydrogen or optionally substituted methyl;

X is optionally substituted aryl or optionally substituted heteroaryl; preferably X is optionally substituted phenyl;

Alternatively, B and X are taken together with the carbon atom to which they are attached to form an optionally substituted $C_4$-$C_{12}$ cycloalkenyl or optionally substituted 4- to 12-membered heterocyclic, for example, a $C_4$-$C_{12}$ cycloalkenyl or 4- to 12-membered heterocyclic which is fused with an aryl or heteroaryl ring wherein each ring is optionally further substituted;

Y is optionally substituted aryl or optionally substituted heteroaryl; preferably Y is optionally substituted azolyl, optionally substituted pyridyl, or optionally substituted phenyl;

Z is selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$C_3$-$C_8$ cycloalkyl, optionally substituted 3- to 8-membered heterocyclic, optionally substituted aryl, optionally substituted heteroaryl, —C(O)NR$_1$R$_2$, and —C(O)OR$_1$;

$R_1$ and $R_2$ at each occurrence are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl;

Alternatively, $R_1$ and $R_2$ are taken together with the nitrogen atom to which they are attached form an optionally substituted 3- to 12-membered heterocyclic;

R is selected from the group consisting of optionally substituted —$C_1$-$C_8$ alkyl, optionally substituted —$C_2$-$C_8$ alkenyl, and optionally substituted —$C_2$-$C_8$ alkynyl;

Alternatively, R and Z are taken together with the atoms to which they are attached to form an optionally substituted 4- to 12-membered heterocyclic; and Alternatively, R and A are taken together with the atoms to which they are attached to form an optionally substituted 5- to 7-membered heterocyclic.

Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.

Compounds of Formula I can have the stereochemistry shown in Formula Ia or Formula Ib.

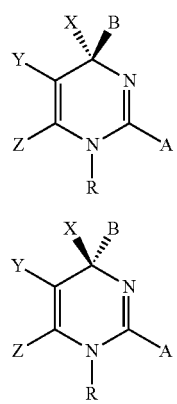

In preferred embodiments, compounds of Formula I have the stereochemistry shown in Formula Ia.

In certain embodiments, the present invention relates to compounds of Formula (I), and pharmaceutically acceptable salts thereof, wherein A is an optionally substituted azolyl, optionally substituted pyridyl, or optionally substituted phenyl.

In certain embodiments, the present invention relates to compounds of Formula (I), and pharmaceutically acceptable salts thereof, wherein Z is hydrogen, optionally substituted —$C_1$-$C_4$ alkyl, or optionally substituted —$C_3$-$C_8$ cycloalkyl.

In certain embodiments, the present invention relates to compounds of Formula (I), and pharmaceutically acceptable salts thereof, wherein Z is an optionally substituted methyl; preferably, Z is a methyl optionally substituted with halo, —OR$_{11}$, or —NR$_{11}$R$_{12}$; wherein R$_{11}$ and R$_{12}$ at each occurrence are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl.

In certain embodiments, the present invention relates to compounds of Formula (I), and pharmaceutically acceptable salts thereof, wherein Z is —C(O)NR$_1$R$_2$ or —C(O)OR$_1$.

In certain embodiments, the present invention relates to compounds of Formula (I), and pharmaceutically acceptable salts thereof, wherein Z is optionally substituted —$C_2$-$C_8$ alkenyl, or optionally substituted —$C_2$-$C_8$ alkynyl.

In certain embodiments, the present invention relates to compounds of Formula (I), and pharmaceutically acceptable salts thereof, wherein Z is optionally substituted 3- to 8-membered heterocyclic.

In certain embodiments, the present invention relates to compounds of Formula (I) and pharmaceutically acceptable salts thereof, wherein Z is selected from the groups set forth below:

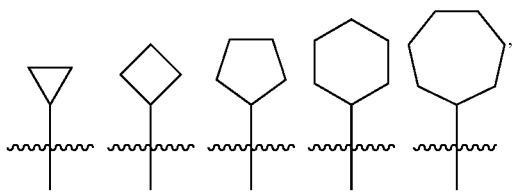

wherein each of the above shown groups is optionally substituted. The preferred substituents include optionally substituted methyl, halo, —CN, =O, =NR$_{11}$, —OR$_{11}$, and —NR$_{11}$R$_{12}$; wherein R$_{11}$ and R$_{12}$ are as previously defined.

In certain embodiments, the present invention relates to compounds of Formula (I), and pharmaceutically acceptable salts thereof, wherein Z is —(CH$_2$)$_n$OR$_{11}$, —(CH$_2$)$_n$OC(O)R$_{11}$, —(CH$_2$)$_n$C(O)OR$_{11}$, —(CH$_2$)$_n$C(O)NR$_{11}$R$_{12}$, —(CH$_2$)$_n$OC(O)OR$_{11}$, —(CH$_2$)$_n$O—C(O)NR$_{11}$R$_{12}$, —(CH$_2$)$_n$NR$_{11}$R$_{12}$, —(CH$_2$)$_n$NR$_{11}$C(O)R$_{11}$, —(CH$_2$)$_n$NR$_{11}$C(O)OR$_{11}$, —(CH$_2$)$_n$NR$_{11}$C(O)—NR$_{11}$R$_{12}$, —(CH$_2$)$_n$S(O)R$_{12}$, —(CH$_2$)$_n$OS(O)$_2$R$_{12}$, —(CH$_2$)$_n$S(O)$_2$OR$_{11}$, —(CH$_2$)$_n$NR$_{11}$S(O)$_2$R$_{12}$, —(CH$_2$)$_n$—S(O)$_2$NR$_{11}$R$_{12}$; —(CH$_2$)$_n$NR$_{11}$S(O)$_2$NR$_{11}$R$_{12}$; —(CH$_2$)$_n$OP(O)(OR$_{11}$)$_2$, —(CH$_2$)$_n$P(O)(OR$_{11}$)$_2$, —(CH$_2$)$_n$—NR$_{11}$P(O)(OR$_{12}$)$_2$, or —(CH$_2$)$_n$P(O)(NR$_{11}$R$_{12}$)$_2$; wherein n is 1, 2, 3, 4, 5, or 6; R$_{11}$ and R$_{12}$ are as previously defined.

In certain embodiments, the present invention relates to compounds of Formula (I), and pharmaceutically acceptable salts thereof, wherein B is hydrogen.

In certain embodiments, the present invention relates to compounds of Formula (I), and pharmaceutically acceptable salts thereof, wherein B is halo, preferably fluoro.

In certain embodiments, the present invention relates to compounds of Formula (I), and pharmaceutically acceptable salts thereof, wherein B is methyl, optionally substituted with one or more halo, preferably fluoro. In certain embodiments, B is difluoromethyl or trifluoromethyl.

In certain embodiments, the present invention relates to compounds of Formula (I), and pharmaceutically acceptable salts thereof, wherein R is optionally substituted —$C_1$-$C_6$ alkyl. In certain embodiments, the present invention relates to compounds of Formula (I), and pharmaceutically acceptable salts thereof, wherein R is optionally substituted —$C_3$-$C_8$ cycloalkyl.

In certain embodiments, the present invention relates to compounds of Formula (I) and pharmaceutically acceptable salts thereof, wherein R is selected from methyl, ethyl, difluoromethyl, trifluoromethyl, —$CH_2CH_2OR_{11}$, —$CH_2CH_2NR_{11}R_{12}$, —$CH_2C(O)R_{11}$, and —$CH_2C(O)NR_{11}R_{12}$.

In certain embodiments, the present invention relates to compounds of Formula (I), and pharmaceutically acceptable salts thereof, wherein R is —$(CH_2)_nOR_{11}$, —$(CH_2)_nOC(O)R_{11}$, —$(CH_2)_nC(O)OR_{11}$, —$(CH_2)_nC(O)NR_{11}R_{12}$, —$(CH_2)_nOC(O)OR_{11}$, —$(CH_2)_nO—C(O)NR_{11}R_{12}$, —$(CH_2)_nNR_{11}R_{12}$, —$(CH_2)_nNR_{11}C(O)R_{11}$, —$(CH_2)_nNR_{11}C(O)OR_{11}$, —$(CH_2)_nNR_{11}C(O)NR_{11}R_{12}$, —$(CH_2)_nS(O)R_{12}$, —$(CH_2)_nOS(O)_2R_{12}$, —$(CH_2)_nS(O)_2OR_{11}$, —$(CH_2)_nNR_{11}S(O)_2R_{12}$, —$(CH_2)_nS(O)_2—NR_{11}R_{12}$, —$(CH_2)_nNR_{11}S(O)_2NR_{11}R_{12}$; —$(CH_2)_nOP(O)(OR_{11})_2$, —$(CH_2)_nP(O)(OR_{11})_2$, —$(CH_2)_nNR_{11}P(O)(OR_{12})_2$, or —$(CH_2)_nP(O)(NR_{11}R_{12})_2$; wherein n, $R_{11}$ and $R_{12}$ are as previously defined.

In certain embodiments, the present invention relates to compounds of Formula (I), and pharmaceutically acceptable salts thereof, wherein X is optionally substituted phenyl. In certain embodiments, the present invention relates to compounds of Formula (I), and pharmaceutically acceptable salts thereof, wherein X is optionally substituted heteroaryl.

In certain embodiments, the present invention relates to compounds of Formula (I) and pharmaceutically acceptable salts thereof, wherein A is optionally substituted thiophenyl, optionally substituted imidazolyl, optionally substituted thiazolyl, optionally substituted oxazolyl, optionally substituted pyridyl.

In certain embodiments, the present invention relates to compounds of Formula (I), and pharmaceutically acceptable salts thereof, wherein Y is optionally substituted phenyl. In certain embodiments, the present invention relates to compounds of Formula (I), and pharmaceutically acceptable salts thereof, wherein Y is optionally substituted heteroaryl. In certain embodiments, the present invention relates to compounds of Formula (I), and pharmaceutically acceptable salts thereof, wherein Y is optionally substituted azolyl or optionally substituted pyridyl.

In certain embodiments, the present invention relates to compounds of Formula (I), and pharmaceutically acceptable salts thereof, wherein X is optionally substituted phenyl; and Y is an optionally substituted heteroaryl. In certain embodiments, the present invention relates to compounds of Formula (I), and pharmaceutically acceptable salts thereof, wherein X is optionally substituted phenyl; and Y is optionally substituted azolyl, optionally substituted pyridyl, or optionally substituted phenyl.

In certain embodiments, the present invention relates to compounds of Formula (I), and pharmaceutically acceptable salts thereof, wherein X is optionally substituted monocyclic heteroaryl; and Y is optionally substituted azolyl, optionally substituted pyridyl, or optionally substituted phenyl.

In another particular embodiment, the present invention relates to compounds of Formula (I), or a pharmaceutically acceptable salt thereof, wherein A and X are each independently an aryl or heteroaryl group derived from one of the following by removal of one hydrogen atom:

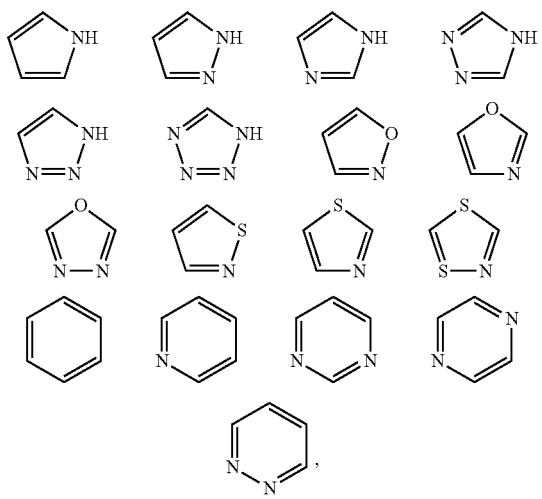

wherein each of the above shown aryl and heteroaryl groups is optionally substituted and is preferably connected to the dihydropyrimidine core through a carbon atom.

In another particular embodiment, the present invention relates to compounds of Formula (I), or a pharmaceutically acceptable salt thereof, wherein at least one of A and X is an aryl or heteroaryl group derived from one of the following by removal of one hydrogen atom:

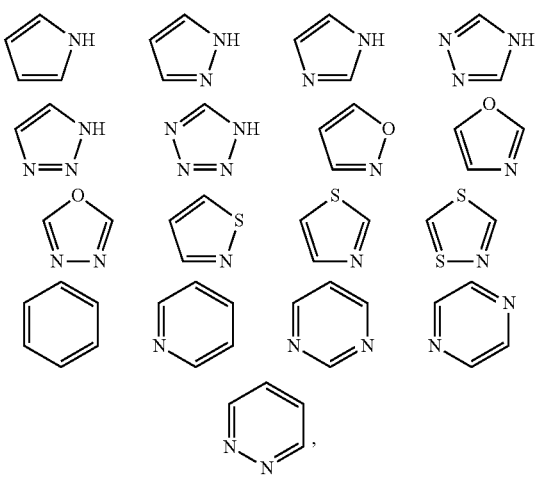

wherein each of the above shown aryl and heteroaryl groups is optionally substituted and is preferably connected to the dihydropyrimidine core through a carbon atom.

In certain embodiments, A and X are each independently selected from the groups set forth below:

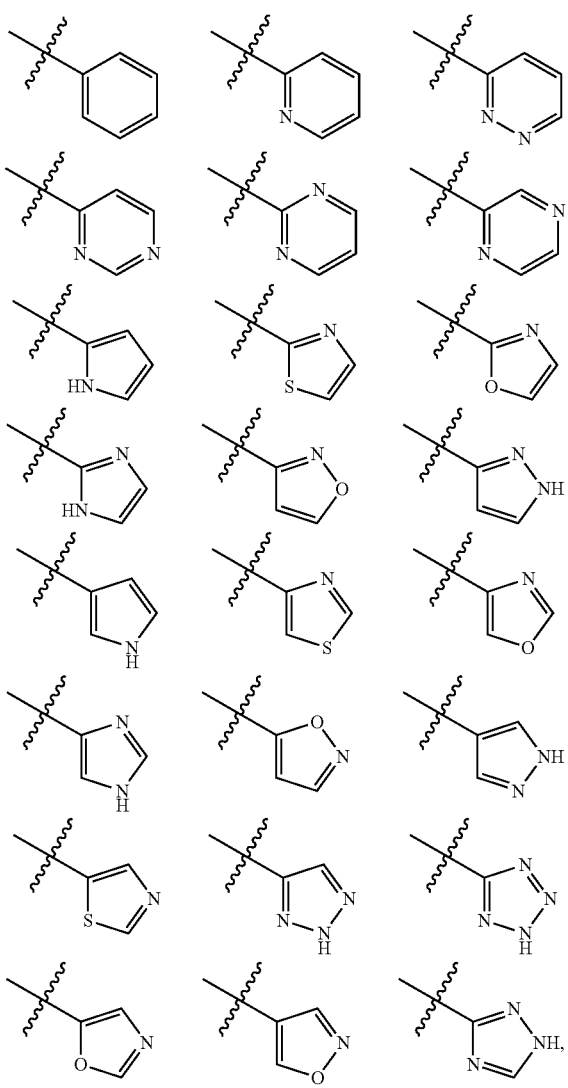

wherein each of the above shown groups is optionally substituted. The preferred substituents are optionally substituted methyl, halo, CN, OR$_{11}$, and —NR$_{11}$R$_{12}$; wherein R$_{11}$ and R$_{12}$ are as previously defined.

In certain embodiments, at least one of A and X is selected from the groups set forth below:

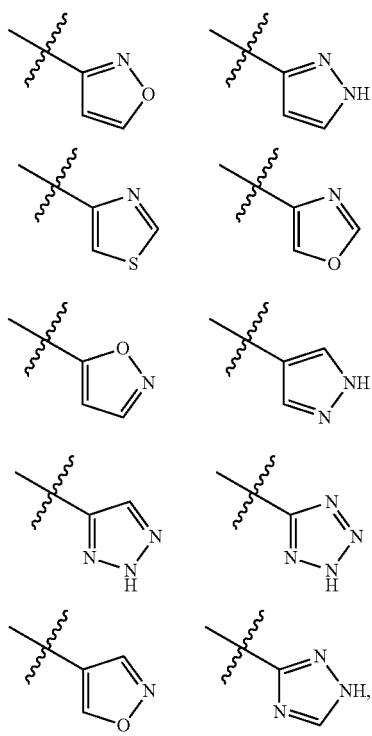

wherein each of the above shown groups is optionally substituted when possible. The preferred substituents are optionally substituted methyl, halo, CN, OR$_{11}$, or —NR$_{11}$R$_{12}$; wherein R$_{11}$ and R$_{12}$ are as previously defined.

In certain embodiments, the present invention relates to compounds of Formula (I) and pharmaceutically acceptable salts thereof, wherein Y is selected from the groups set forth below:

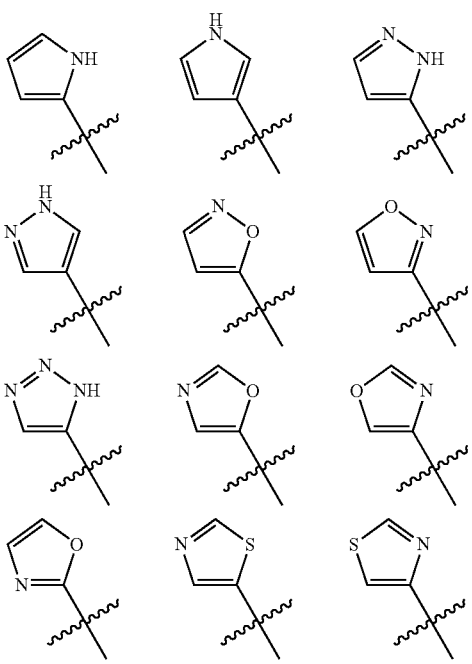

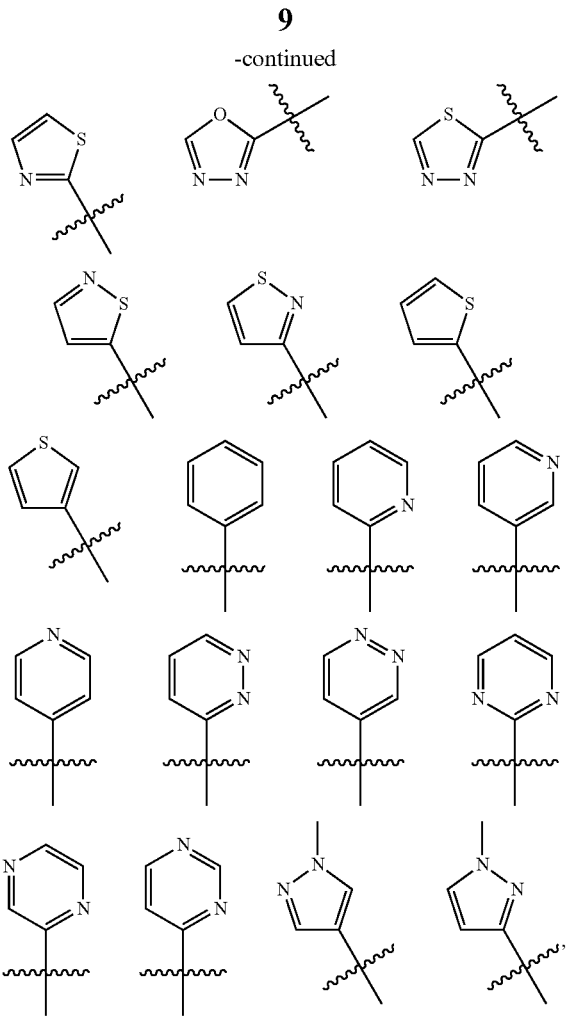

wherein each of the above shown groups is optionally substituted. The preferred substituents include optionally substituted methyl, halo, —CN, —OR$_{11}$, and —NR$_{11}$R$_{12}$; wherein R$_{11}$ and R$_{12}$ are as previously defined.

In certain embodiments, the present invention relates to compounds of Formula (I) and pharmaceutically acceptable salts thereof, wherein Y is optionally substituted azolyl.

In certain embodiments, the present invention relates to compounds of Formula (I) and pharmaceutically acceptable salts thereof, wherein Y is selected from the groups set forth below:

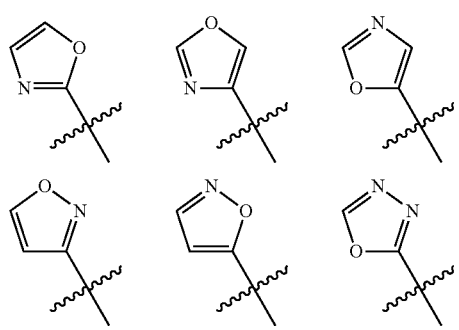

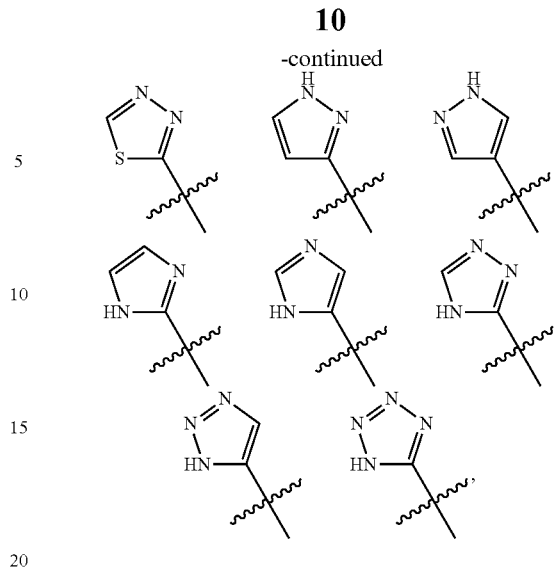

wherein each of the above shown groups is optionally substituted when possible.

In certain embodiments, the present invention relates to compounds of Formula (I) and pharmaceutically acceptable salts thereof, wherein Y is selected from the groups set forth below:

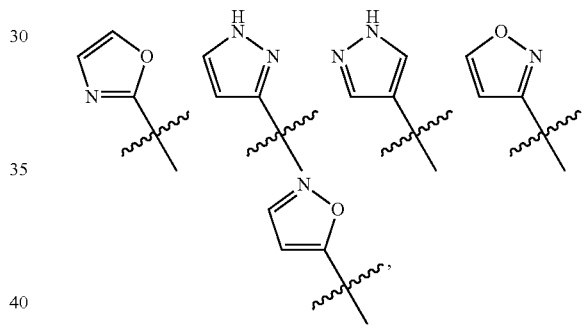

wherein each of the above shown groups is optionally substituted. The preferred substituents include optionally substituted —C$_1$-C$_4$-alkyl, halo, —CN, —OR$_{11}$, and —NR$_{11}$R$_{12}$; R$_{11}$ and R$_{12}$ are as previously defined.

In certain embodiments, the present invention relates to compounds of Formula (I) and pharmaceutically acceptable salts thereof, wherein Y is selected from the groups set forth below:

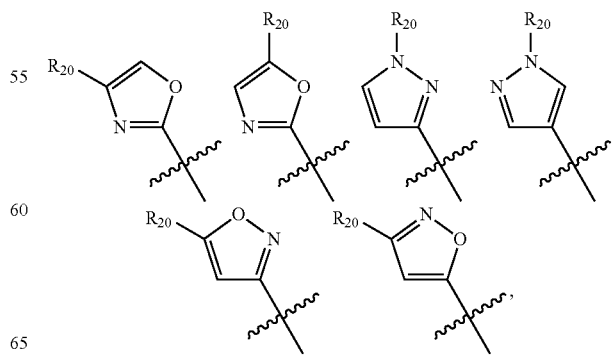

wherein $R_{20}$ is optionally substituted $C_1$-$C_4$-alkyl or $C_3$-$C_6$-cycloalkyl. Preferably, $R_{20}$ is optionally substituted methyl or optionally substituted cyclopropyl.

In certain embodiments, the present invention relates to compounds of Formula (I) and pharmaceutically acceptable salts thereof, wherein Z is —$(CH_2)_{n'}$-M; wherein n' is 1, 2, or 3; M is hydrogen, —$OR_{11}$, protected hydroxy, —$CR_{11}R_{12}R_3$, —$NR_{11}R_{12}$, protected amino or selected from the groups set forth below:

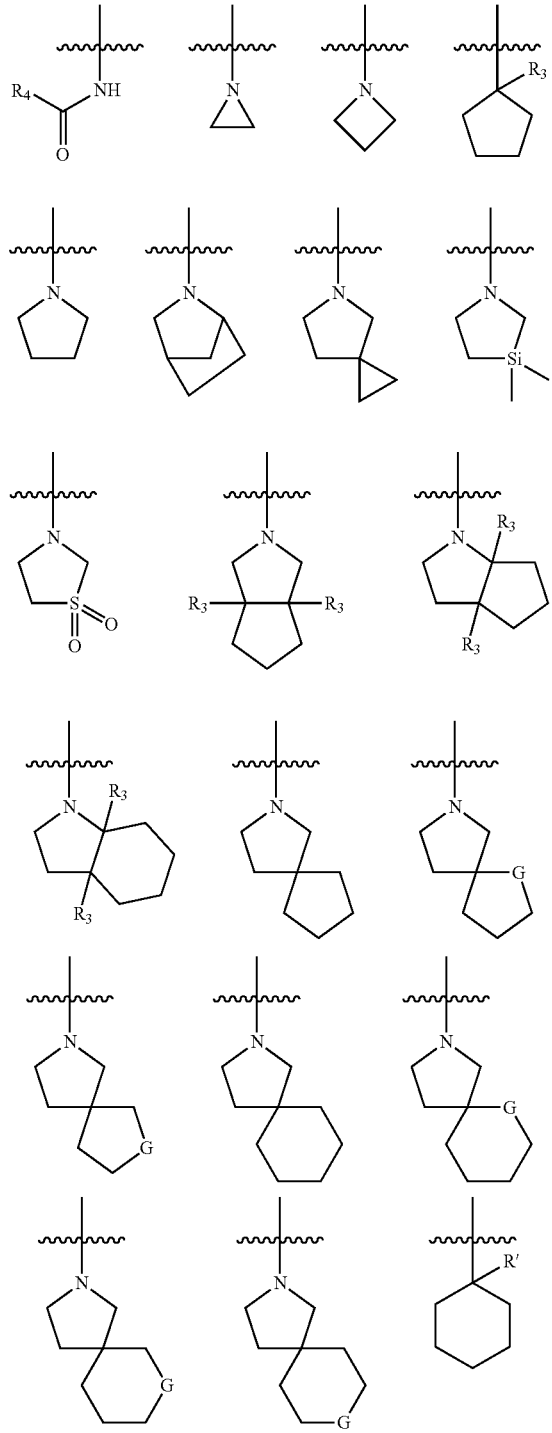

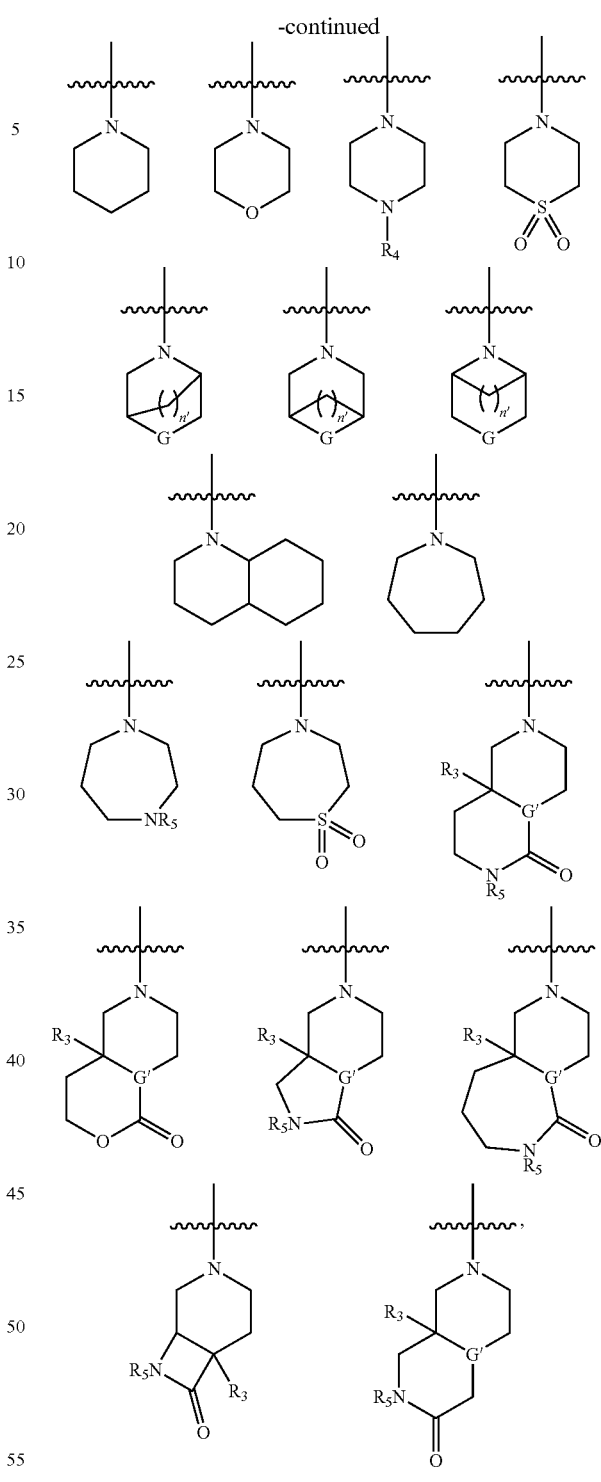

wherein each of the above shown groups is optionally substituted; the preferred substituents include halo, =O, =$NR_{11}$, —$OR_{11}$, —$NR_{11}R_{12}$, —CN, —$CO_2R_{11}$, —C(O)$NR_{11}R_{12}$, and optionally substituted methyl; $R_3$ is selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, —CN, —$OR_{11}$, and —$NR_{11}R_{12}$; $R_4$ is selected from the group consisting of —$NR_{11}R_{12}$, $OR_{11}$, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; $R_5$ is selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl, optionally substituted heteroaryl, —C(O)$R_{11}$, —C(O)O$R_{11}$, —C(O)N$R_{11}R_{12}$, —S(O)$_2R_{11}$, —S(O)$_2$N$R_{11}R_{12}$; G is independently selected from C$R_{11}R_{12}$, O and N$R_5$; G' is independently selected from C$R_5$ and N; and n', $R_{11}$ and $R_{12}$ are as previously defined. In certain embodiments, $R_5$ is selected from the groups set forth below:

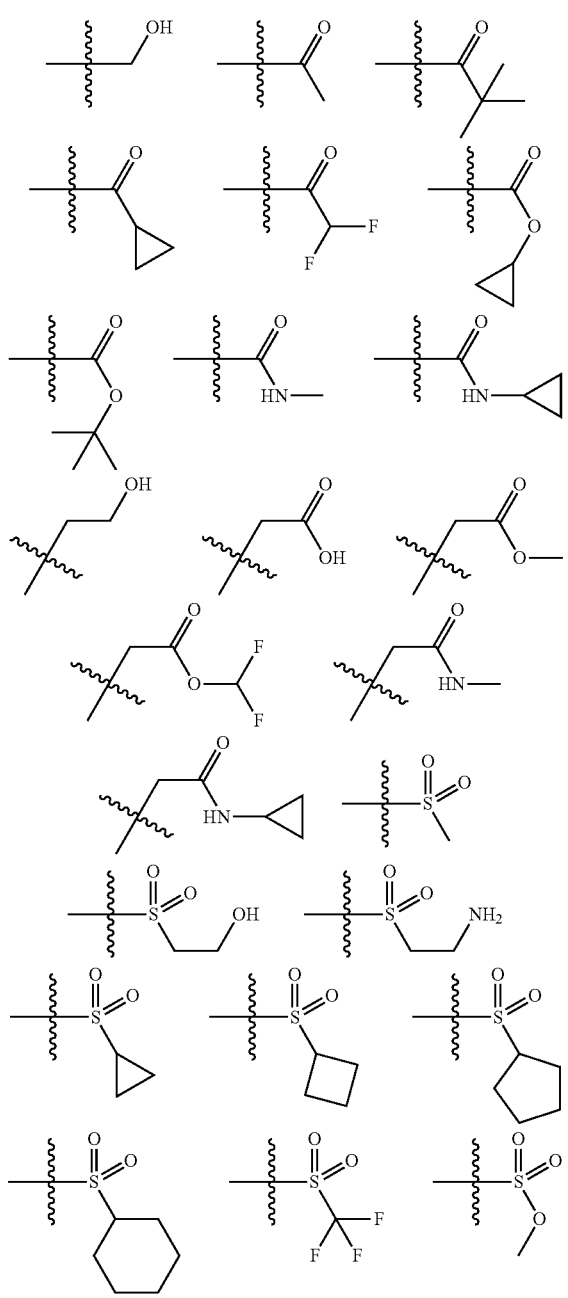

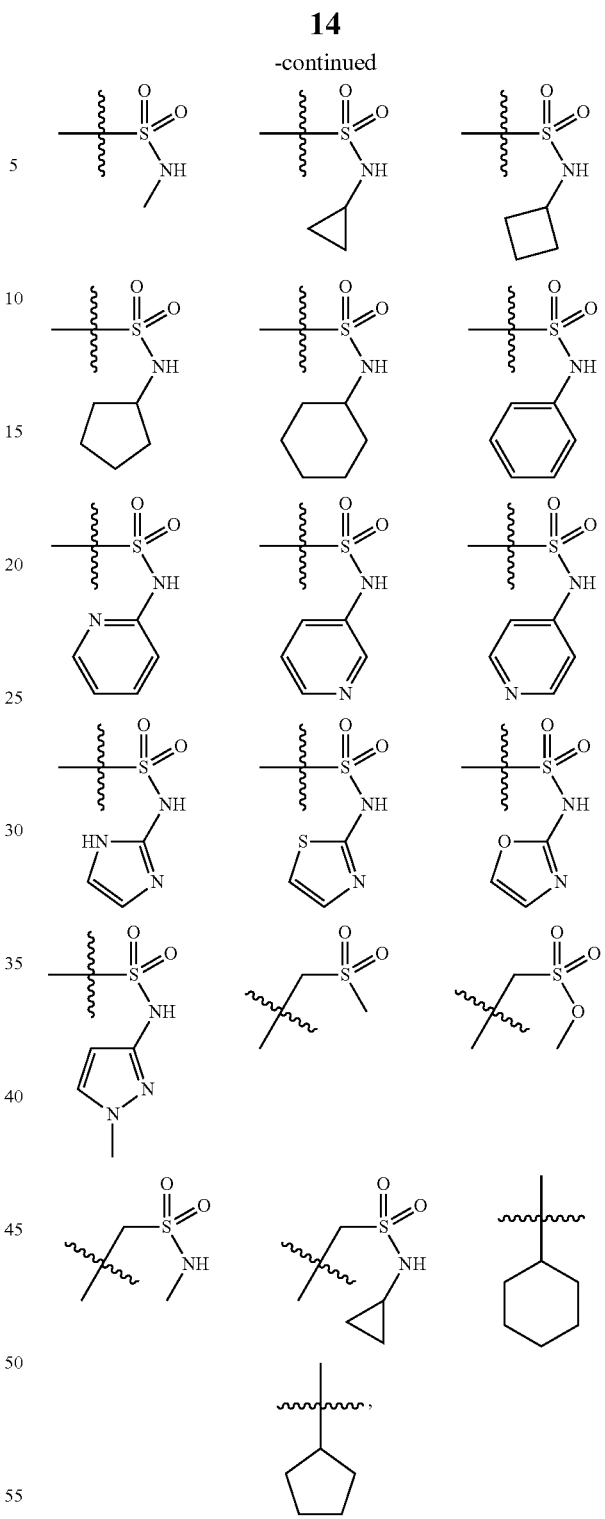

wherein each of the above shown groups is optionally substituted; the preferred substituents include halo, —O$R_{11}$, —N$R_{11}R_{12}$, —CN, —CO$_2R_{11}$, —C(O)N$R_{11}R_{12}$, optionally substituted methyl, and optionally substituted phenyl. In another embodiment, $R_5$ is —SO$_2$NH$_2$.

In another embodiment, the present invention relates to compounds of Formula (I) and pharmaceutically acceptable salts thereof, wherein Z is —(CH$_2$)$_n$-M, preferably —CH$_2$-M, wherein M is selected from the groups set forth below:

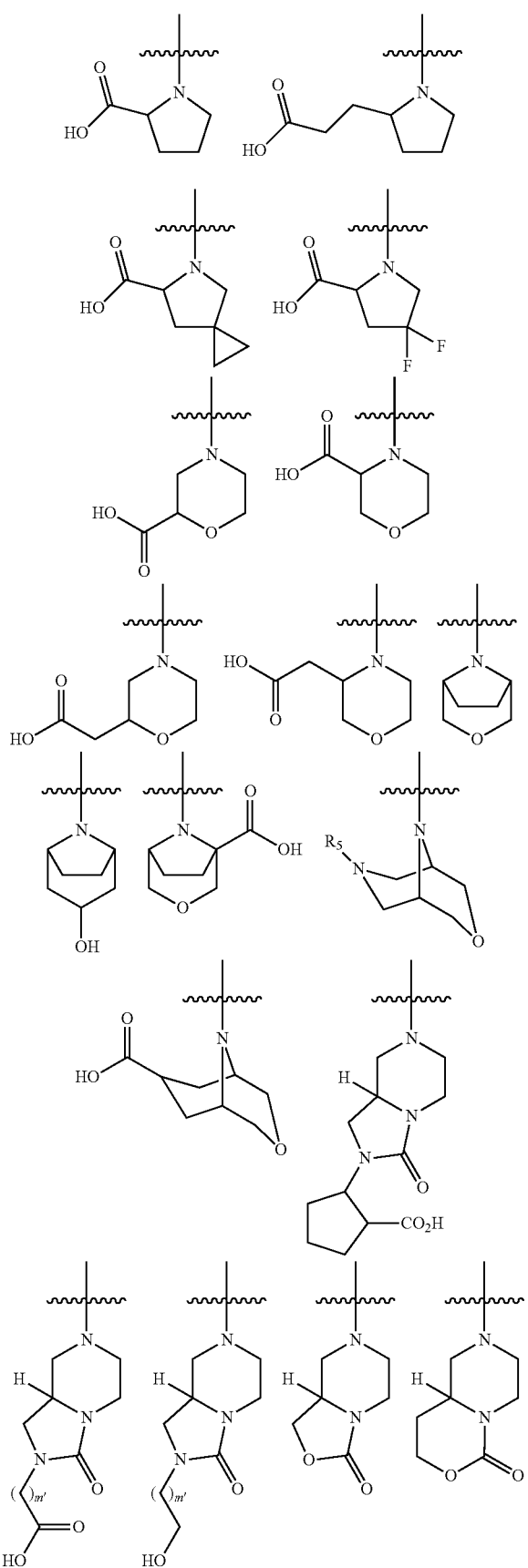

wherein each of the above shown groups is optionally substituted when possible; the preferred substituents include halo, —OR$_{11}$, —NR$_{11}$R$_{12}$, —CN, —CO$_2$R$_{11}$, —C(O)NR$_{11}$R$_{12}$, optionally substituted methyl, and optionally substituted phenyl; m' is 1, 2, or 3; and n', R$_{11}$, R$_{12}$, and R$_5$ are as previously defined.

In another embodiment, the compound of Formula (I) is represented by Formula (IIa) or (IIb) or a pharmaceutically acceptable salt thereof:

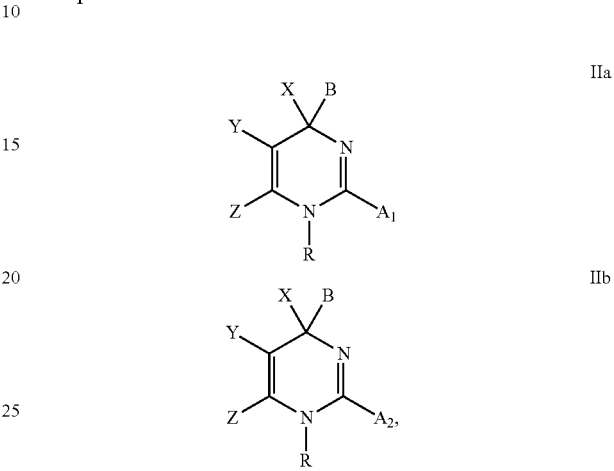

wherein A$_1$ is a 5-membered heteroaryl group containing 1 to 4 heteroatoms selected from O, N, and S; preferably A$_1$ is an optionally substituted azole group including but not limited to pyrrolyl, pyrazolyl, imidazolyl, thiazolyl, oxazolyl, isooxazolyl, thiadiazolyl, oxadiazolyl; each optionally substituted; A$_2$ is an optionally substituted phenyl, thiophenyl or 6-membered heteroaryl group including but not limited to pyridinyl, pyrazinyl, or pyrimidinyl; each optionally substituted; B, R, X, Y, and Z are as previously defined.

In another embodiment, the compound of Formula (I) is represented by Formula (IIa-1) or (IIb-1), or a pharmaceutically acceptable salt thereof:

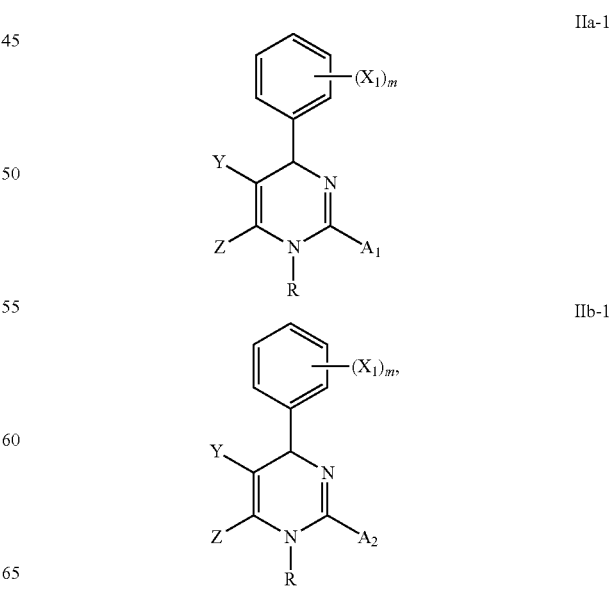

wherein $X_1$ is optionally substituted methyl, halo, CN, $OR_{11}$, or $NR_{11}R_{12}$; m is 0, 1, 2, 3, 4 or 5; $A_1$, $A_2$, R, Y, Z, $R_{11}$, and $R_{12}$ are as previously defined.

In certain embodiments, the compound of Formula (I) is represented by Formula (IIa-1) or (IIb-1), or a pharmaceutically acceptable salt thereof, wherein m is 0 or m is 1-5 and each $X_1$ is halo. In certain embodiments, the compound of Formula (I) is represented by Formula (IIa-1) or (IIb-1), or a pharmaceutically acceptable salt thereof, wherein Y is optionally substituted azolyl. In another embodiment, the compound of Formula (I) is represented by Formula (IIa-1) or (IIb-1), or a pharmaceutically acceptable salt thereof, wherein Z is hydrogen or optionally substituted methyl.

In certain embodiments, the compound of Formula (I) is represented by Formula (IIa-1) or (IIb-1), or a pharmaceutically acceptable salt thereof, wherein R is selected from the group consisting of —$(CH_2)_nOR_{11}$, —$(CH_2)_nOC(O)R_{11}$, —$(CH_2)_nC(O)OR_{11}$, —$(CH_2)_nC(O)NR_{11}R_{12}$, —$(CH_2)_nOC(O)OR_{11}$, —$(CH_2)_nO$—$C(O)NR_{11}R_{12}$, —$(CH_2)_nNR_{11}R_{12}$, —$(CH_2)_nNR_{11}C(O)R_{11}$, —$(CH_2)_nNR_{11}C(O)OR_{11}$, —$(CH_2)_n NR_{11}C(O)NR_{11}R_{12}$, —$(CH_2)_nS(O)R_{12}$, —$(CH_2)_nOS(O)_2 R_{12}$, —$(CH_2)_nS(O)_2OR_{11}$, —$(CH_2)_nNR_{11}S(O)_2 R_{12}$, —$(CH_2)_nS(O)_2NR_{11}R_{12}$; —$(CH_2)_nNR_{11}S(O)_2 NR_{11}R_{12}$; —$(CH_2)_nOP(O)(OR_{11})_2$, —$(CH_2)_nP(O)(OR_{11})_2$, —$(CH_2)_n NR_{11}P(O)$—$(OR_{12})_2$, and —$(CH_2)_nP(O)(NR_{11}R_{12})_2$; preferably, R is —$(CH_2)_nOR_{11}$; and n, $R_{11}$ and $R_{12}$ are as previously defined.

In certain embodiments, the compound of Formula (I) is represented by Formula (IIa-1) or (IIb-1), or a pharmaceutically acceptable salt thereof, wherein Z is selected from the group consisting of —$(CH_2)_nOR_{11}$, —$(CH_2)_nOC(O)R_{11}$, —$(CH_2)_nC(O)OR_{11}$, —$(CH_2)_nC(O)NR_{11}R_{12}$—$(CH_2)_nOC(O)OR_{11}$, —$(CH_2)_nO$—$C(O)NR_{11}R_{12}$, —$(CH_2)_nNR_{11}R_{12}$, —$(CH_2)_nNR_{11}C(O)R_{11}$, —$(CH_2)_nNR_{11}C(O)OR_{11}$, —$(CH_2)_n NR_{11}C(O)NR_{11}R_{12}$, —$(CH_2)_nS(O)R_{12}$, —$(CH_2)_nOS(O)_2 R_{12}$, —$(CH_2)_nS(O)_2OR_{11}$, —$(CH_2)_nNR_{11}S(O)_2R_{12}$, —$(CH_2)_nS(O)_2NR_{11}R_{12}$; —$(CH_2)_nNR_{11}S(O)_2NR_{11}R_{12}$; —$(CH_2)_nOP(O)(OR_{11})_2$, —$(CH_2)_nP(O)(OR_{11})_2$, —$(CH_2)_n NR_{11}P(O)$—$(OR_{12})_2$, and —$(CH_2)_nP(O)(NR_{11}R_{12})_2$; preferably, Z is —$(CH_2)_nNR_{11}S(O)_2R_{12}$; and n, $R_{11}$ and $R_{12}$ are as previously defined.

In another embodiment, the compound of Formula (I) is represented by Formula (IIa-2), or (IIb-2), or a pharmaceutically acceptable salt thereof:

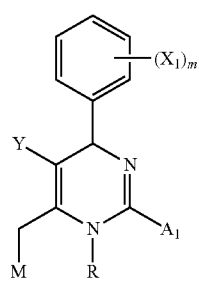

IIa-2

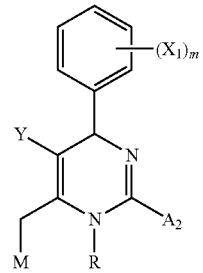

IIb-2 wherein $X_1$, m, $A_1$, $A_2$, R, Y, M, $R_3$, $R_{11}$ and $R_{12}$ are as previously defined.

In another embodiment, the compound of Formula (I) is represented by Formula (IIa-2) or (IIb-2), or a pharmaceutically acceptable salt thereof, wherein M is —$CR_{11}R_{12}R_3$, or —$NR_{11}R_{12}$; wherein $R_{11}$ and $R_{12}$ are taken together with the atom to which they are attached to form an optionally substituted $C_3$-$C_8$ mono-cycloalkyl or an optionally substituted 3- to 8-membered mono-heterocyclic, wherein said cycloalkyl or heterocyclic contains 0 to 3 substituents independently selected from =$CR_{13}R_{14}$, =O, and =$NR_{13}$; $R_{13}$ and $R_{14}$ are each independently selected from the group consisting of hydrogen, halo, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; alternatively, $R_{13}$ and $R_{14}$ are taken together with the carbon atom to which they are attached to form an optionally substituted $C_3$-$C_8$ cycloalkyl; $R_3$ is as previously defined.

In yet another embodiment, the compound of Formula (I) is represented by Formula (IIa-2) or (IIb-2), or a pharmaceutically acceptable salt thereof, wherein M is —$CR_{11'}R_{12'}R_3$, or —$NR_{11'}R_{12'}$; wherein $R_{11'}$ and $R_{12'}$ are taken together with the atom they are attached to form an optionally substituted $C_5$-$C_{12}$ bi- or tri-cycloalkyl or an optionally substituted 5- to 12-membered bi- or tri-heterocyclic, wherein said optionally substituted $C_5$-$C_{12}$ bi- or tri-cycloalkyl or an optionally substituted 5- to 12-membered bi- or tri-heterocyclic comprises a first ring which includes the carbon atom to which $R_{11'}$, $R_{12'}$ and $R_3$ are attached or the nitrogen atom to which $R_{11'}$ and $R_{12'}$ are attached, a second ring and an optional third ring, wherein the second ring is (1) spiro attached to the first ring, (2) fused to the first ring or (3) formed by a 1,3- or 1,4-bridging group between two ring atoms of the first ring. Preferably, the first ring is a 3-, 4-, 5-, 6- or 7-membered ring. $R_3$ is as previously defined.

In yet another embodiment, the compound of Formula (I) is represented by Formula (IIa-2) or (IIb-2), or a pharmaceutically acceptable salt thereof, wherein R is selected from the group consisting of —$(CH_2)_nOR_{11}$, —$(CH_2)_nOC(O)R_1$, —$(CH_2)_nC(O)OR_1$, —$(CH_2)_nC(O)$—$NR_{11}R_{12}$, —$(CH_2)_n OC(O)OR_{11}$, —$(CH_2)_nO$—$C(O)NR_{11}R_{12}$, —$(CH_2)_n NR_{11}R_{12}$, —$(CH_2)_nNR_{11}C(O)R_{11}$, —$(CH_2)_nNR_{11}C(O)OR_{11}$, —$(CH_2)_nNR_{11}C(O)NR_{11}R_{12}$, —$(CH_2)_nS(O)R_{12}$, —$(CH_2)_nOS(O)_2R_{12}$, —$(CH_2)_nS(O)_2OR_{11}$, —$(CH_2)_n NR_{11}S(O)_2R_{12}$, —$(CH_2)_nS(O)_2NR_{11}R_{12}$; —$(CH_2)_nNR_{11}S(O)_2NR_{11}R_{12}$; —$(CH_2)_nOP(O)(OR_{11})_2$, —$(CH_2)_nP(O)(OR_{11})_2$, —$(CH_2)_nNR_{11}P(O)(OR_{12})_2$, and —$(CH_2)_nP(O)$—$(NR_{11}R_{12})_2$; n, $R_{11}$ and $R_{12}$ are as previously defined.

In another embodiment, the compound of Formula (I) is represented by Formula (IIa-3) or (IIb-3), or a pharmaceutically acceptable salt thereof:

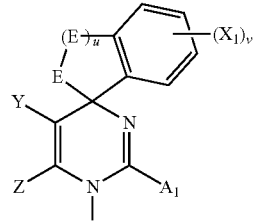

IIa-3

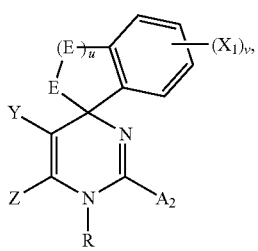

IIb-3 wherein E at each occurrence is the same or different and independently selected from —CR$_{15}$R$_{16}$—, —C(O)—, —O—, —NR$_{16}$—, —S—, and —S(O)$_2$—; u is 0, 1, 2, or 3; R$_{15}$ is hydrogen, halo, CN, —NR$_{11}$R$_{12}$, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocyclic, optionally substituted aryl and optionally substituted heteroaryl; R$_{16}$ is hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocyclic, optionally substituted aryl and optionally substituted heteroaryl; alternatively, R$_{15}$ and R$_{16}$ are taken together with the carbon atom to which they are attached to form an optionally substituted C$_3$-C$_7$ cycloalkyl or an optionally substituted 3- to 7-membered heterocyclic; v is 0, 1, 2, 3, or 4; X$_1$, A$_1$, A$_2$, R, Y, Z, R$_{11}$, and R$_{12}$ are as previously defined.

In certain embodiments, the present invention relates to compounds of Formula (IIa-3) or (IIb-3) and pharmaceutically acceptable salts thereof, wherein two vicinal E groups are taken together to form an optionally substituted C=C double-bond or an optionally substituted fused ring. In certain embodiments, two non-adjacent E groups are taken together to form a bridging group.

In another embodiment, the compound of Formula (I) is represented by Formula (IIIa) or (IIIb), or a pharmaceutically acceptable salt thereof,

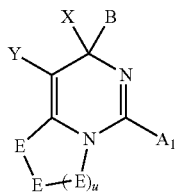

IIIa

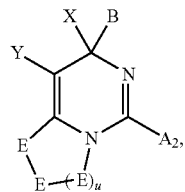

IIIb wherein u, B, X, A$_1$, A$_2$, Y, and E, are as previously defined.

In certain embodiments, the present invention relates to compounds of Formula (IIIa) or (IIIb) and pharmaceutically acceptable salts thereof, wherein two vicinal E groups are taken together to form a C=C double-bond, a C=N double-bond or a fused ring. In certain embodiments, two remote E groups are taken together to form a bridging group.

In certain embodiments, the present invention relates to compounds of Formula (IIIa) or (IIIb) or pharmaceutically acceptable salts thereof, wherein

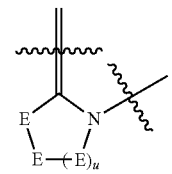

is selected from the groups set forth below:

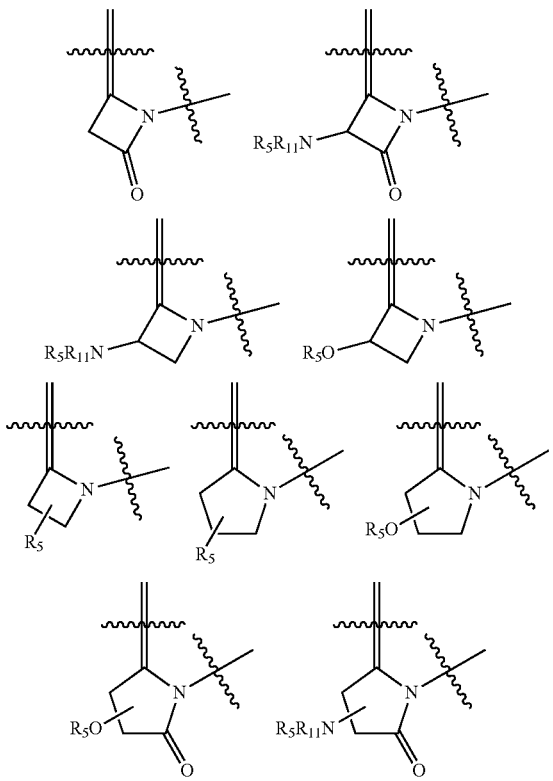

-continued

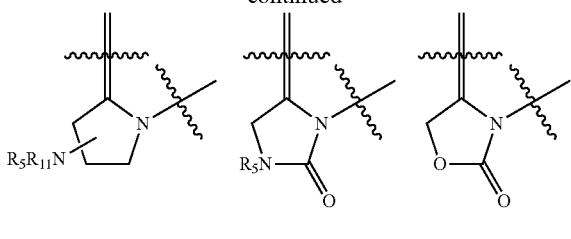
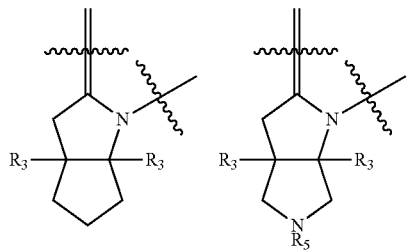
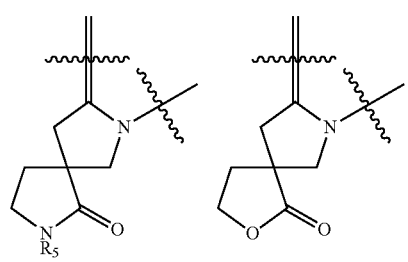
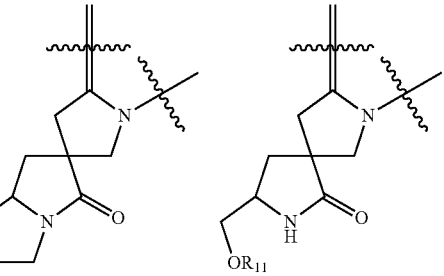
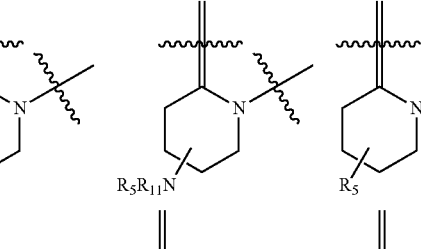
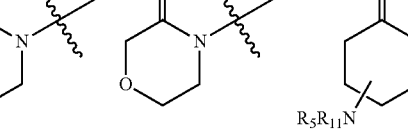
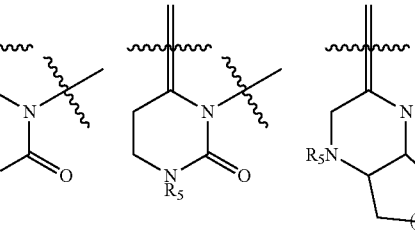

-continued

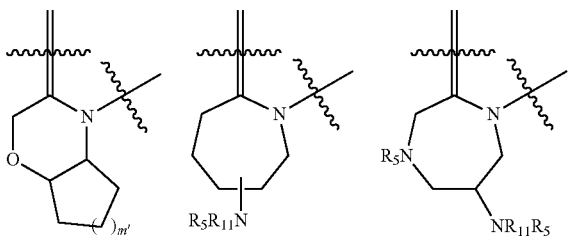
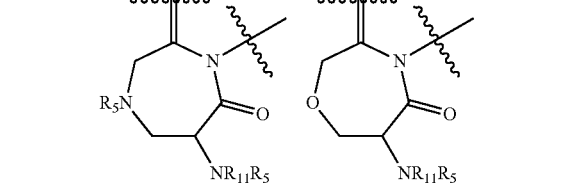
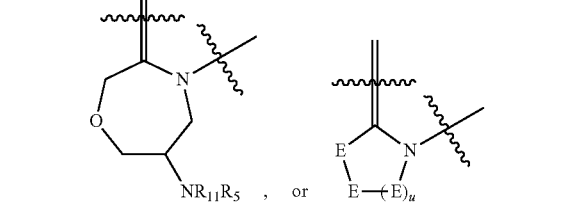
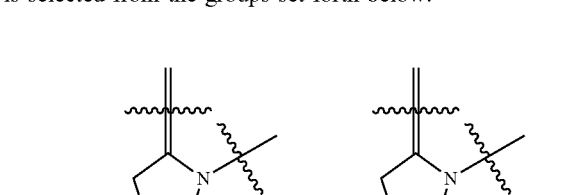
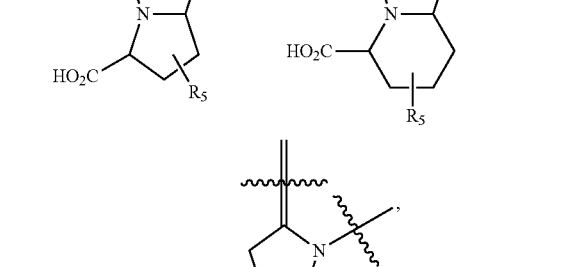

is selected from the groups set forth below:

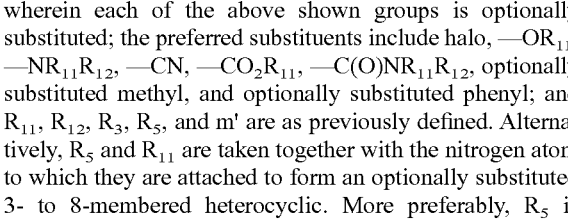

wherein each of the above shown groups is optionally substituted; the preferred substituents include halo, —OR$_{11}$, —NR$_{11}$R$_{12}$, —CN, —CO$_2$R$_{11}$, —C(O)NR$_{11}$R$_{12}$, optionally substituted methyl, and optionally substituted phenyl; and R$_{11}$, R$_{12}$, R$_3$, R$_5$, and m' are as previously defined. Alternatively, R$_5$ and R$_{11}$ are taken together with the nitrogen atom to which they are attached to form an optionally substituted 3- to 8-membered heterocyclic. More preferably, R$_5$ is selected from the groups set forth below:

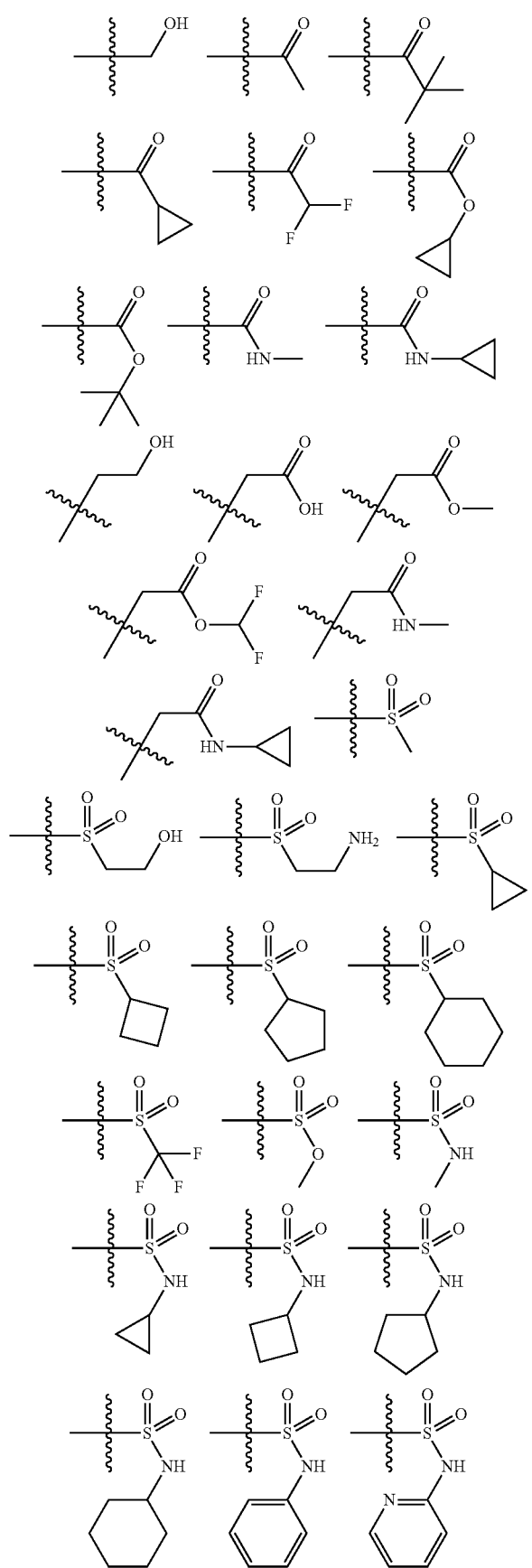

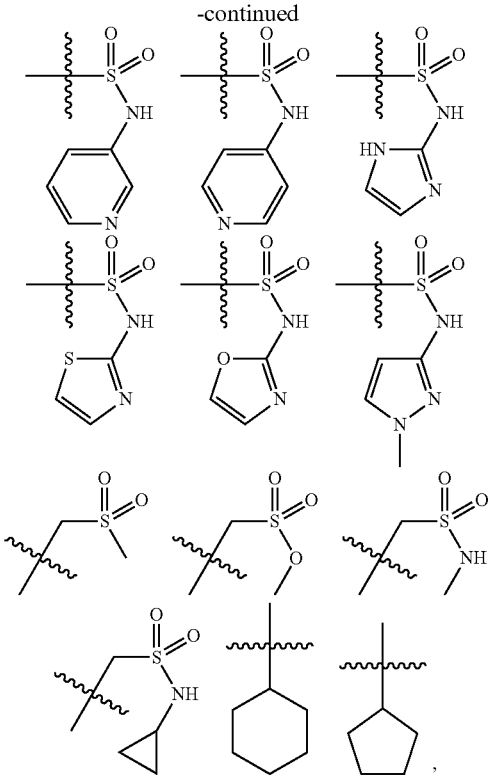

wherein each of the above shown groups is optionally substituted when possible; the preferred substituents include halo, —$OR_{11}$, —$NR_{11}R_{12}$, —CN, —$CO_2R_{11}$, —$C(O)NR_{11}R_{12}$, optionally substituted methyl, and optionally substituted phenyl. In another embodiment, $R_5$ is —$SO_2NH_2$.

In certain embodiments, the compound of Formula (I) is represented by Formula (IIIa-1) or (IIIb-1), or a pharmaceutically acceptable salt thereof,

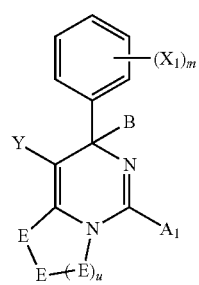

wherein $A_1$, $A_2$, $X_1$, m, B, Y, E, and u are as previously defined.

In certain embodiments, the compound of Formula (I) is represented by Formula (IIIa-2) or (IIIb-2), or a pharmaceutically acceptable salt thereof,

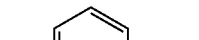

IIIa-2

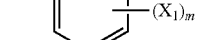

IIIb-2 wherein $A_1$, $A_2$, $X_1$, m, Y, E, and u are as previously defined.

In certain embodiment, the compound of Formula (I) is represented by Formula (IIIa-3) or (IIIb-3), or a pharmaceutically acceptable salt thereof,

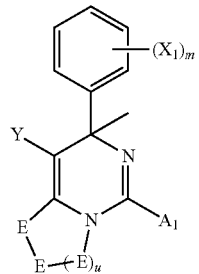

IIIa-3

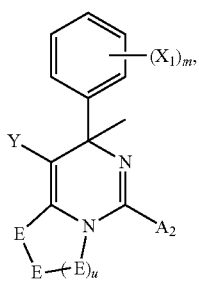

IIIb-3 wherein $A_1$, $A_2$, $X_1$, m, Y, E, and u are as previously defined.

In certain embodiment, the compound of Formula (I) is represented by Formula (IIIa-4) or (IIIb-4), or a pharmaceutically acceptable salt thereof,

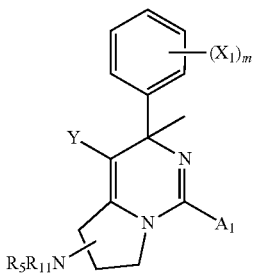

IIIa-4

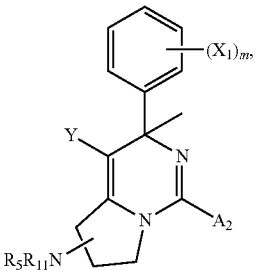

IIIb-4 wherein $A_1$, $A_2$, $X_1$, m, Y, $R_5$ and $R_{11}$ are as previously defined.

In certain embodiments, the compound of Formula (I) is represented by Formula (IIIa-4) or (IIIb-4), or a pharmaceutically acceptable salt thereof, wherein $A_1$, $A_2$, $X_1$, m, $R_5$ and $R_{11}$ are as previously defined, and Y is optionally substituted azolyl. Preferably Y is optionally substituted pyrazolyl or oxazolyl.

In certain embodiments, the compound of Formula (I) is represented by Formula (IIIa-5) or (IIIb-5), or a pharmaceutically acceptable salt thereof,

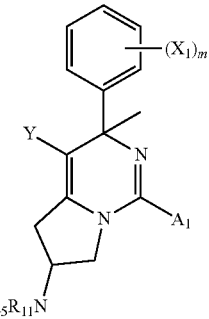

IIIa-5

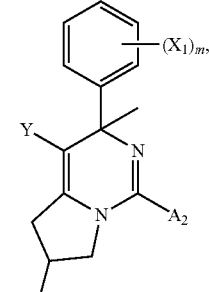

IIIb-5 wherein $A_1$, $A_2$, $X_1$, m, Y, $R_5$ and $R_{11}$ are as previously defined.

In certain embodiments, the compound of Formula (I) is represented by Formula (IIIa-5) or (IIIb-5), or a pharmaceutically acceptable salt thereof, wherein $A_1$, $A_2$, $X_1$, m, $R_5$ and $R_{11}$ are as previously defined, and Y is optionally substituted azolyl. Preferably Y is optionally substituted pyrazolyl or oxazolyl.

In certain embodiments, the compound of Formula (I) is represented by Formula (IIIa-6) or (IIIb-6), or a pharmaceutically acceptable salt thereof,

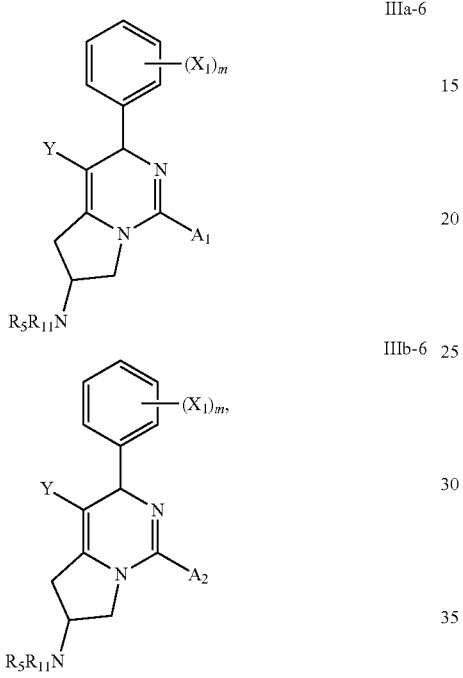

IIIa-6

IIIb-6 wherein $A_1$, $A_2$, $X_1$, m, Y, $R_5$ and $R_{11}$ are as previously defined.

In certain embodiments, the compound of Formula (I) is represented by Formula (IIIa-6) or (IIIb-6), or a pharmaceutically acceptable salt thereof, wherein $A_1$, $A_2$, $X_1$, m, $R_5$ and $R_{11}$ are as previously defined, and Y is optionally substituted azolyl. Preferably Y is optionally substituted pyrazolyl or oxazolyl.

In another embodiment, the compound of Formula (I) is represented by Formula (IV), or a pharmaceutically acceptable salt thereof,

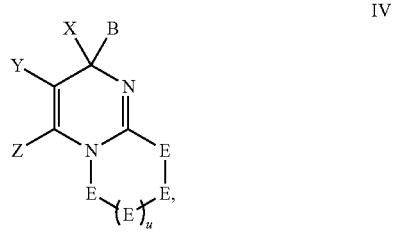

IV wherein, B, X, Y, Z, E and u are as previously defined.

In yet another embodiment, the compound of Formula (I) is represented by Formula (IVa) (IVb), (IVc), or a pharmaceutically acceptable salt thereof,

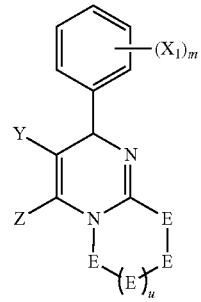

IVa

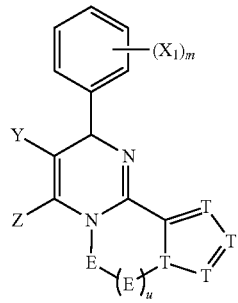

IVb

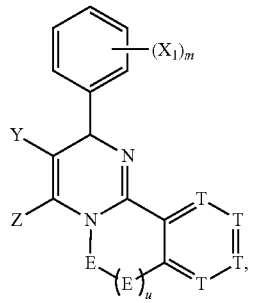

IVc wherein each T is independently —$CR_{15}$, or N; $X_1$, m, Y, Z, E, u, and $R_{15}$ are as previously defined. Preferably $R_{15}$ is H, halo, methyl or $CF_3$.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA. In another embodiment, the additional therapeutic agent is selected from immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein, or RNA interence (RNAi) or small interfering RNA (siRNA) such as ARC-520, ARC-521, ARB-1467, and ALN-HBV RNAi, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139. In an embodiment of the combination therapy, the reverse transcriptase inhibitor is at least one of Zidovudine, Didanosine, Zalcitabine, ddA, Stavudine, Lamivudine, Aba-cavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl)propyl]amino Imethyl)phenyl]acetate), GS-9620 (4-Amino-2-butoxy-8-[3-(1-pyrrolidinylmethyl)benzyl]-7,8-dihydro-6 (5H)-pteridinone), and RO6864018.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "azole group," as used herein, refers to 5-membered heteroaromatic ring containing at least one nitrogen atom. Preferred azole groups contain a nitrogen atom and at least one additional heteroatom, preferably a nitrogen, oxygen or sulfur atom. Azole groups include, but are not limited to pyrazolyl, imidazolyl, thiazolyl, oxazolyl, isoxazolyl, 1,2,3-triazolyl, 1,2,4-triazolyl, tetrazolyl. An azole group is termed "ortho" substituted in reference to two substituents which are on adjacent ring atoms. An azole group is termed "meta" substituted in reference to two substituents which are not on adjacent ring positions.

The term "bicyclic azole" or "bicyclic azole group" refers to an aromatic ring system consisting of two rings wherein at least one ring is azole group; and the two rings can be fused or covalently attached. Preferred bicyclic azole groups are those in which an azole ring is fused to a six-membered aromatic or heteroaromatic ring. Such groups include, but are not limited to, benzimidazolyl, benzopyrazolyl, benzotriazolyl, benzoxazolyl, benzisoxazolyl, benzothiazolyl, imidazolopyridyl, pyrazolopyridyl, thiazolopyridyl, oxazolopyridyl, isoxazolopyridyl, triazolopyridyl, and tetrazolopyridyl.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O— heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$— aryl, $CO_2$-heteroaryl, $CO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$— heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH— heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Combination and Alternation Therapy

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combination are selected from the group consisting of a HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; Boc$_2$O for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; Bu$_3$SnH for tributyltin hydride; BOP for (benzotriazol-1-yloxy)tris(dimethylamino)phospho-nium Hexafluorophosphate; Brine for sodium chloride solution in water; BSA for N,O-bis(trimethylsilyl)acetamide; CDI for carbonyldiimidazole; DCM or CH$_2$Cl$_2$ for dichloro-methane; CH$_3$ for methyl; CH$_3$CN for acetonitrile; Cs$_2$CO$_3$ for cesium carbonate; CuCl for copper (I) chloride; CuI for copper (I) iodide; dba for dibenzylidene acetone; dppb for diphenylphosphinobutane; DBU for 1,8-diazabicyclo[5.4.0]-undec-7-ene; DCC for N,N'-dicyclohexyl-carbodiimide; DEAD for diethylazodicarboxylate; DIAD for diisopropyl azodicarboxylate; DIPEA or (i-Pr)$_2$EtN for N,N-diisopropylethyl amine; Dess-Martin periodinane for 1,1,1-tris(acetyloxy)-1,1-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; DMT for di(p-methoxyphenyl)-phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; Et$_2$O for diethyl ether; HATU for O-(7-azabenzotriazol-1-yl)-N,N,N',N'-tetramethyluronium Hexafluoro-phosphate; HCl for hydrogen chloride; HOBT for 1-hydroxybenzotriazole; K$_2$CO$_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethyl-piperidinate; MeOH for methanol; Mg for magnesium; MOM for methoxymethyl; Ms for mesyl or —SO$_2$—CH$_3$; Ms$_2$O for methanesulfonic anhydride or mesyl-anhydride; MTBE for t-butyl methyl ether; NaN(TMS)$_2$ for sodium bis(trimethylsilyl) amide; NaCl for sodium chloride; NaH for sodium hydride; NaHCO$_3$ for sodium bicarbonate or sodium hydrogen carbonate; Na$_2$CO$_3$ sodium carbonate; NaOH for sodium hydroxide; Na$_2$SO$_4$ for sodium sulfate; NaHSO$_3$ for sodium bisulfite or sodium hydrogen sulfite; Na$_2$S$_2$O$_3$ for sodium thiosulfate; NH$_2$NH$_2$ for hydrazine; NH$_4$HCO$_3$ for ammonium bicarbonate; NH$_4$Cl for ammonium chloride; NMO for N-methylmorpholine N-oxide; NaIO$_4$ for sodium periodate; Ni for nickel; OH for hydroxyl; OsO$_4$ for osmium tetroxide; PPA for polyphophoric acid; PTSA for p-toluenesulfonic acid; PPTS for pyridinium p-toluenesulfonate; PhI(OPiv)$_2$ for Bis(tert-butylcarbonyloxy)iodobenzene; Rh$_2$(Esp)$_2$ for Bis[rhodium(α,α,α',α'-tetramethyl-1,3-benzenedipropionic acid)]; TBAF for tetrabutylammonium fluoride; TEA or Et$_3$N for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or PPh$_3$ for triphenyl-phosphine; Troc for 2,2,2-trichloroethyl carbonyl; Ts for tosyl or —SO$_2$—C$_6$H$_4$CH$_3$; Ts$_2$O for tolylsulfonic anhydride or tosyl-anhydride; TsOH for p-tolylsulfonic acid; Pd for palladium; Ph for phenyl; POPd for dihydrogen dichlorobis(di-tert-butylphosphinito-KP)palladate(II); Pd$_2$(dba)$_3$ for tris(dibenzylideneacetone) dipalladium (0); Pd(PPh$_3$)$_4$ for tetrakis (triphenylphosphine)-palladium (0); PdCl$_2$(PPh$_3$)$_2$ for transdichlorobis-(triphenylphosphine)palladium (II); Pt for platinum; Rh for rhodium; rt for room temperature; Ru for ruthenium; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

The nature of the group B in Formula I will have a significant effect on the choice of the synthesis methods, as demonstrated below.

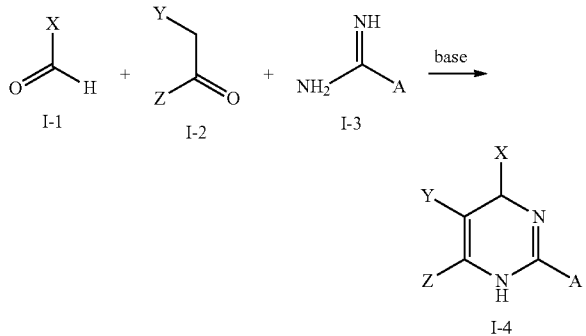

Scheme 1

When B in Formula I is a hydrogen, an illustrative method is shown in Schemes 1, the X, A, Y, Z are as defined as previously for formula I. The starting material aldehyde I-1, a ketone I-2 wherein Y is an electron withdrawing group, such as an ester, or an aromatic group (the desired aryl or heteroaryl) and an amidine I-3 are all either commercially available or can be easily prepared by those familiar with the skill of the arts. The dihydropyrimidine core I-4 can be prepared in one pot process from an aldehyde I-1, a ketone I-2 and an amidine I-3 (or its salt) in the presence of a suitable base as such potassium acetate or potassium bicarbonate in a solvent like methanol, or trifluoroethanol. Most frequently, elevated temperature is required for this transformation. Starting from this core I-4, A, X, Y, Z could be individually manipulated and converted to varieties of functional groups.

For instance, when Z in I-4 is a methyl, this methyl can be further functionalized easily. One specific example is shown in scheme 1a, when I-4a is treated with NBS, the methyl bromide I-5 will be obtained. The bromide can be displaced with nucleophiles. Therefore, when I-5a is reacted with various bi-functional molecules Z'(CH$_2$)$_m$GH, in which GH is a nucleophile, such as an amine, an alcohol or a malonate; Z' is precursor of a leaving group, such as a protected hydroxyl or a ester, in the presence of a suitable base such as TEA or pyridine, will provide a more complicated structure I-6a. Next the Z' is converted to a desired leaving group by either de-protection or reduction to free the alcohol, followed by mesylate formation to afford the 1-7a. Alternatively, bromide or tosylate may be used. When 1-7a is treated with a base, like TEA or K$_2$CO$_3$, in a proper solvent such as THF, acetonitrile or DMF will give the cyclized product 1-8a.

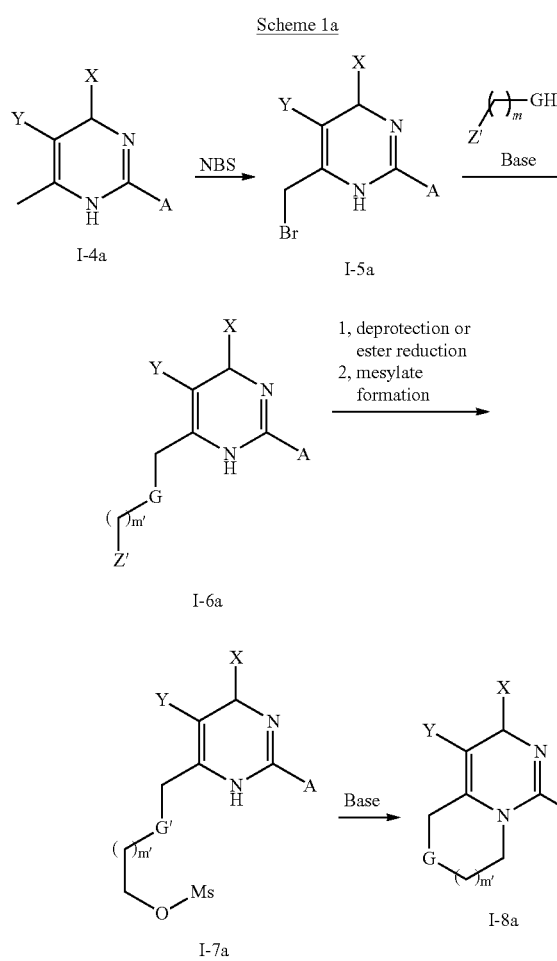

Scheme 1a

Next, Y in the formula I-8a can be further manipulated. For instance, as shown in Scheme 1b, wherein Y is an ester, R$_3$ is as defined as previously. In the case while R$_3$ is t-Butyl or allyl, then ester I-8b can be converted to an advanced carboxyl acid intermediate I-9b when treated with strong acid (HCl or TFA) or Pd(PPh$_3$)$_4$/Morpholine, respectively. By taking advantage of this carboxyl acid as a key intermediate, various functional groups can be generated from it. One specific example is shown in the same scheme, this carboxyl acid is converted to the acyl chloride followed by treating with amines to give the amide I-10b. Alternatively this transformation also can be completed in the presence of a dehydration reagent such as EDC or DCC as well as a base like TEA, DIPEA. When R$_1$ and R$_2$ are hydrogen, this amide when treated with a dehydration reagent such as TFAA will afford a nitrile. This nitrile can serve as advanced intermediate for azoles. When R$_1$ is methyl, R$_2$ is methoxyl, a Weinreb amide is obtained. In the next step, this Weinreb amide is reduced to an aldehyde or reacted with all sorts of Grignard reagent will offer various ketone, which could serve as later stage intermediate for further functional group manipulation for more complicated heteroaryl including azoles. One example is shown in the same scheme, the Weinreb amide I-10b can be reduced to afford the aldehyde I-11b, which when reacted with acetone in the presence of a base such as LDA will offer the α,β-unsaturated ketone 1-12b. I-12b is treated with hydroxyl amine followed by an iodine induced cyclization to afford the isoxazole I-13c. More related arts can be found in the various publications (for example, J. A Joule and K. Mills, *Heterocyclic Chemistry*, 5$^{th}$ edition, 557 and reference therein). G, m' and R$_3$ are as previously defined.

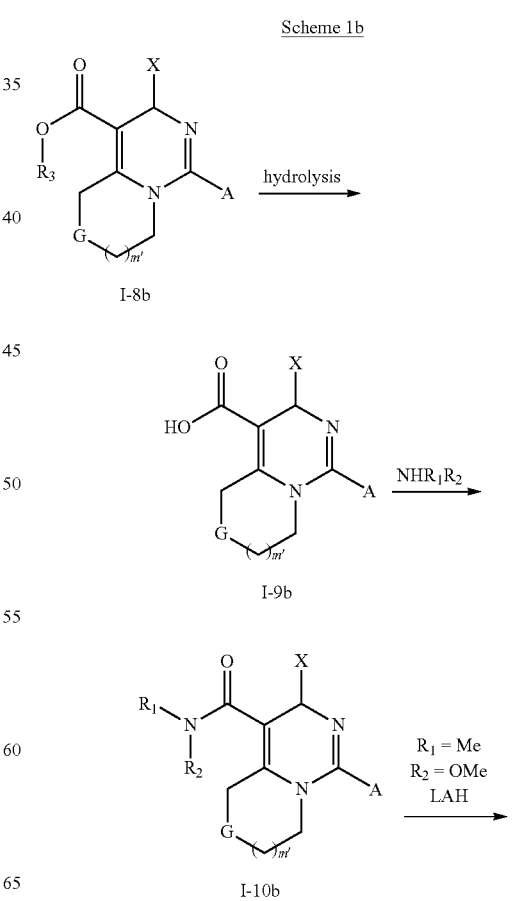

Scheme 1b treated with at least two equivalents of NBS, the di-bromo compound I-7d will be obtained. Starting from this di-bromo I-7d, following similar chemical procedure described in Scheme 1a for converting I-5a to I-8a, the 5-bromo compound I-10c will be generated. From it, target I-11c will be obtained as discussed in Scheme 1c.

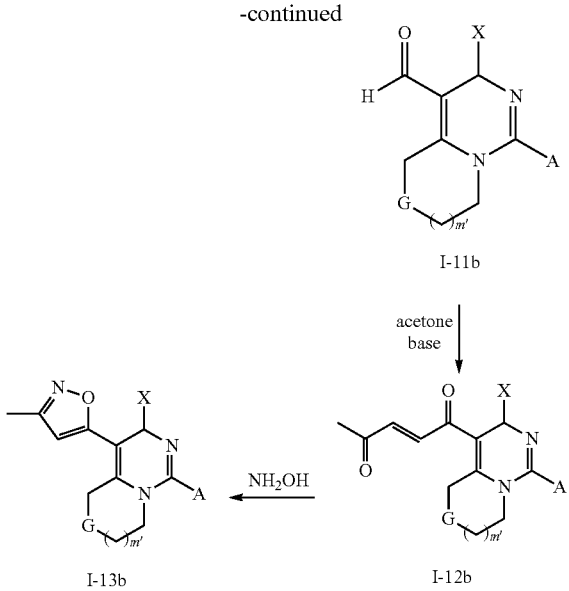

In yet another specific example as shown in Scheme 1c, when the carboxyl acid I-9b is treated with pyridinium tribromide in the presence a base such as pyridine, a bromide I-10c will be produced. The bromide reacts with various aryl or heteroaryl boronic ester/acid or tin reagent, which can be commercial available or easily prepared by those familiar with the skill of the arts, under the Pd(0) catalyzed coupling conditions to give the target molecule I-11c. (see reviews: A. Suzuki, Pure Applied Chem., 1991, 63, 419; A. Suzuki, Handbook of Organopalladium Chemistry for Organic Synthesis, 2002, 1, 249; A. Anastasia, et al, Handbook of Organopalladium Chemistry for Organic Synthesis, 2002, 1, 311).

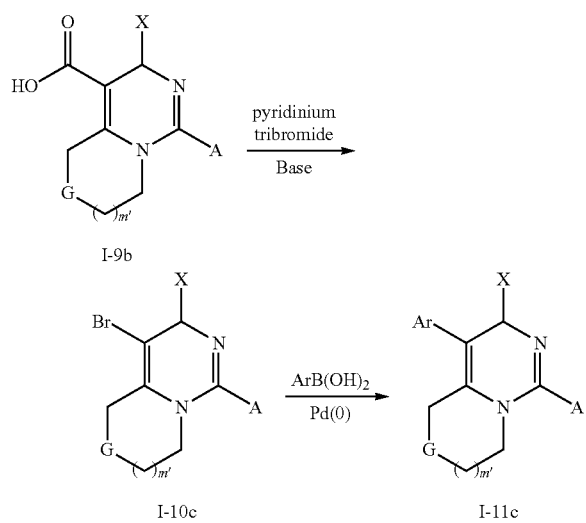

In yet another specific example as shown Scheme 1d, the compound I-4d can be protected with a proper protecting group such as Boc, or Cbz to give I-5d. Hydrolysis the ester of I-5d following similar procedure as described in Scheme 1b will afford the acid I-6d. When the carboxyl acid I-6d is

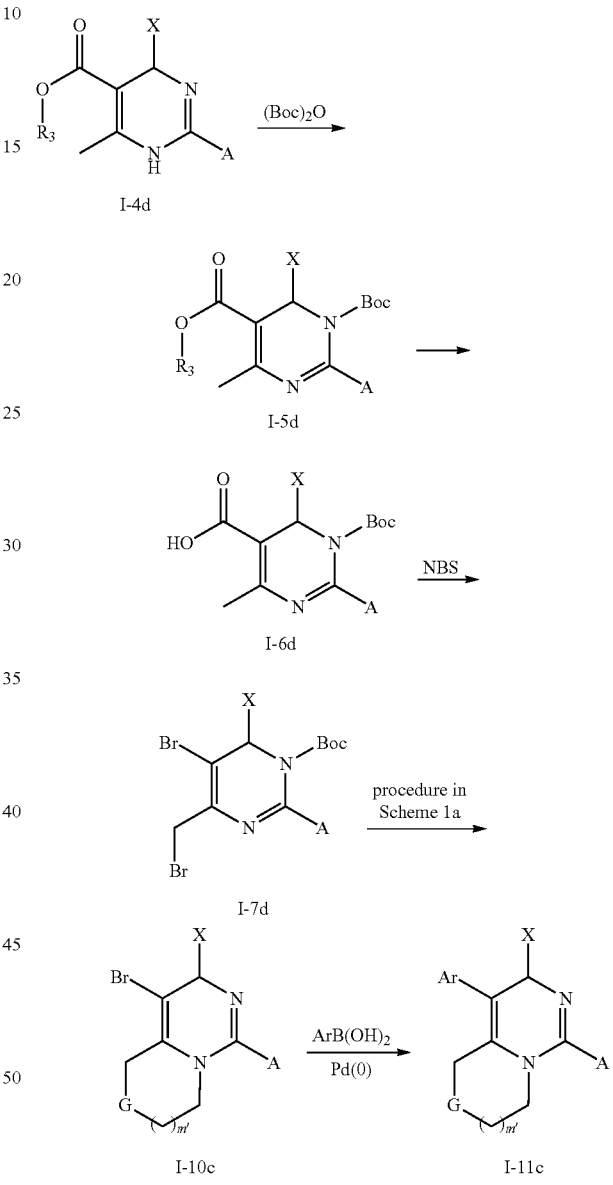

In yet another specific example as shown Scheme 1e, if the amidine I-3 shown in Scheme 1 is replaced with a urea, a dihydropyrimidine-2-one I-4a analogue to I-4 is generated. It is well known in literature (A. Karnail, et al, Journal of Organic Chemistry, 1989, 54, 5898) that when this family molecules are treated with (Boc)$_2$O in the present of a base such as TEA, or DIPEA, a N-3 Boc protected product I-5e will be obtained. Alkylation of this intermediate I-5e with an alkylation reagent, like RBr with the desired R group in the presence of a proper base such as NaH will afford the N-1 alkylated intermediate I-6e. When I-6e is treated with an acid, like HCl or TFA, the N-3 Boc protecting group will be removed, which is followed by heating this material in POCl₃ to lead to the 2-chloro dhydropyrimidine I-7e. This chloride reacts with various aryl or heteroaryl boronic ester/acid or tin reagent, which can be commercial available or easily prepared by those familiar with the skill of the arts, under the Pd(0) catalyzed coupling conditions to give the target molecule I-8e contains the desired A group. When I-8e is reacted with 1 equivalent NBS, the 6-methyl will be brominated to offer advanced intermediated I-9e. The bromide in I-9e can be displaced with the desired M group with MH in the presence of proper base to afford I-10e. In molecule I-10e, if the Y is desired aryl or heteroaryl group, then I-10e is a desired target; if Y is an ester, then all the chemistry described in Scheme 1b and Scheme 1c can be applied to afford the desired product. R and M are as previously defined.

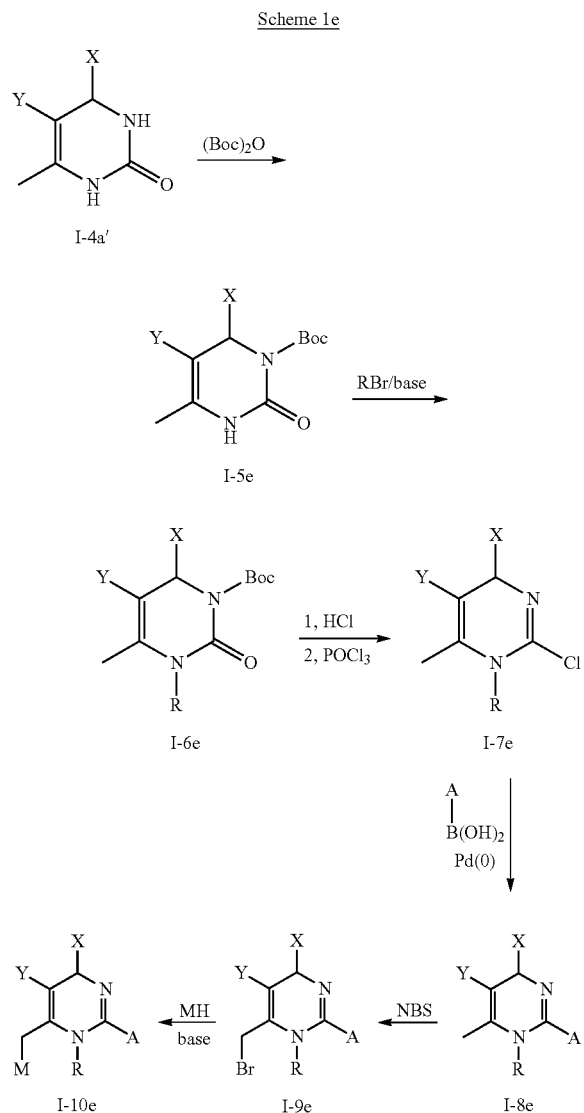

On the other hand, if the R in I-9e contains a nucleophile such as I-9e' as shown in Scheme 1f, when treated with a base, TEA, or NaH will afford the intermediate I-8a.

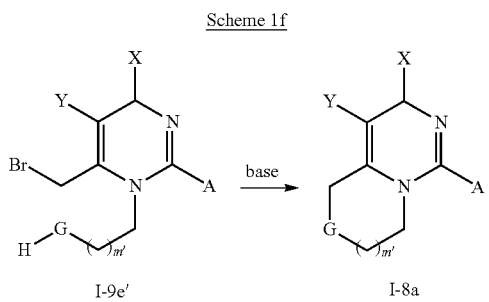

On the other hand when B is CN or an alkyl group, a stepwise route is required for the preparation of the final targets. As illustrated in Scheme 2, aldehyde I-1 and I-2 are reacted with each other in the presence of a catalyst system, such as piperidine/acetic acid to afford the α,β-unsaturated ketone II-1. This α,β-unsaturated ketone II-1 reacts with a copper reagent CuB, which can be commercially available or can be easily generated in situ from CuI and BMgX (or BLi). The newly formed α,β-unsaturated ketone II-2 then reacts with I-3 in a similar process described above as in the one-pot process to afford the desired target I.

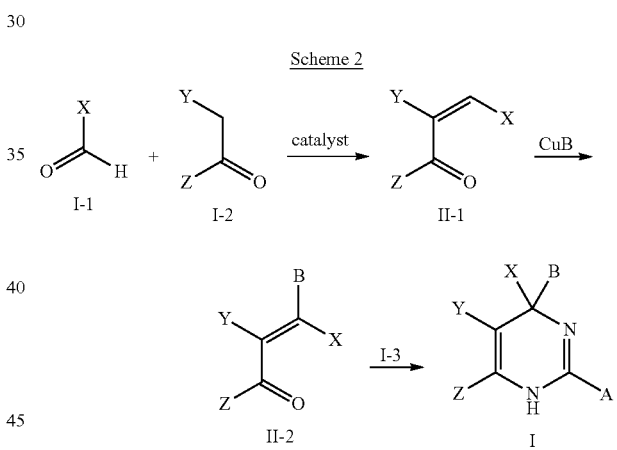

In a specific example, while B is a methyl, X is a aryl or heteroaryl, I in Scheme 2 can be introduced with a chemistry described in Scheme 2a following similar published precedents (For example, WO 2013/102655). A distal acetylene I-1a served as a methyl ketone equivalent reacts with ketone I-2 in the presence of InCl₃ will provide the α,β-unsaturated ketone II-1a, which in turn when reacts with amidine I-3 will provide Ia, the 4-methyl analogue of I.

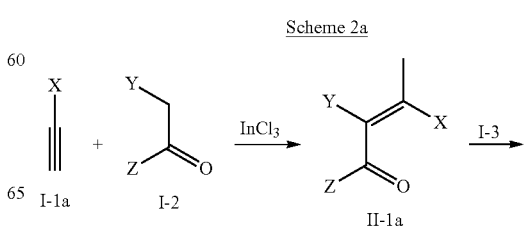

-continued

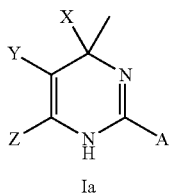

Ia

With I in hand, all the chemistry described in Scheme 1a to Scheme 1f can be applied here to give the desired targets.

Alternatively, in certain cases, even when B is hydrogen, a step wise procedure similar as in Scheme 2 is required to achieve the targets.

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention.

Intermediate 1

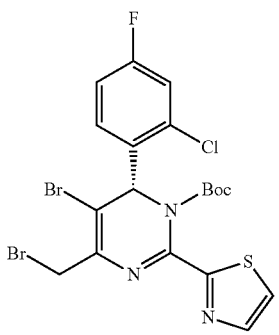 [SMILES: CC(C)(C)OC(=O)N1C(c2nccs2)=NC(CBr)=C(Br)[C@@H]1c1ccc(F)cc1Cl]

Step 1-1a

A solution of ethyl (R)-2-hydroxypropanoate (5 g, 42.3 mmol) and 2,2,6-trimethyl-4H-1,3-dioxin-4-one (6 g, 42.3 mmol) was stirred for 4 hours at 120° C. The mixture was concentrated under vacuum to give desired product (9 g, crude) as yellow oil, which was used in the next step without further purification. ESI MS m/z=203.25 [M+H]$^+$.

Step 1-1b

A solution of the compound from step 1-1a (5 g, 24.5 mmol), 2-chloro-4-fluorobenzaldehyde (4.3 g, 27.3 mmol), TsOH (cat) and HOAc (cat) in toluene (60 mL) was stirred at 110° C. overnight. The mixture was concentrated. The residue was chromatographed (silica, ethyl acetate/petroleum ether) to give the desired product (5.93 g, 70.0%) as yellow solid. ESI MS m/z=343.00 [M+H]$^+$.

Step 1-1c

A solution of the compound from step 1-1b (5 g, 14.6 mmol), thiazole-2-carboximidamide HCl salt (2.38 g, 14.6 mmol) and $K_2CO_3$ (2.01 g, 14.6 mmol) in DMF (20 mL) was stirred for 2 hours at 80° C. It was diluted with EtOAc and washed with brine, filtered and concentrated. After the residue was purified by silica gel column (ethyl acetate/petroleum ether), the mixture was recrystallized from EtOH at 0° C. to give the desired product as yellow solid (1.25 g, 25.0%). ESI MS m/z=452.05 [M+H]$^+$.

Step 1-1d

A solution of the compound from step 1-1c (950 mg, 2.10 mmol), (Boc)$_2$O (915.6 mg, 4.20 mmol) and DMAP (307 mg, 2.51 mmol) in DCM (30 mL) was stirred for 1 hour at rt. The reaction mixture was concentrated. The residue was chromatographed (silica, ethyl acetate/petroleum ether) to give the desired compound as yellow solid (1.07 g, 92%). ESI MS m/z=552.30 [M+H]$^+$.

Step 1-1e

A solution of the compound from step 1-1d (965 mg, 1.75 mmol) in a solution of NaOH [40 mL, 2M in H$_2$O/MeOH (1:5)] was stirred for 18 hours at rt. After being acidified with aq HCl (4N) to pH 5, the mixture was extracted with DCM. The organic layer was washed with aq. NH$_4$Cl and H$_2$O, dried (Na$_2$SO$_4$) and concentrated. The residue was chromatographed (silica, ethyl acetate/petroleum ether) to give the desired compound as yellow solid (620 mg, 78%). ESI MS m/z=452.15 [M+H]$^+$.

Step 1-1f

A solution of the compound from step 1-1e (250 mg, 0.55 mmol) in DCM (10 mL) was treated with NBS (295 mg, 1.66 mmol) for 6 hours at rt. The reaction was quenched by the addition of water (2 mL) and extracted with DCM. The organic layer was dried (Na$_2$SO$_4$), concentrated. The residue was chromatographed (Cis column, MeCN/H$_2$O) to give the title compound as yellow solid (103.5 mg, 33%). ESI MS m/z=566.10, 568.10 [M+H]$^+$. $^1$H NMR (400 MHz, DMSO-d$_6$) δ 8.04 (m, 2H), 7.98 (d, 1H), 7.57 (m, 1H), 7.23 (m, 1H), 6.35 (s, 1H), 4.45 (m, 2H), 1.15 (s, 9H).

Intermediate 2

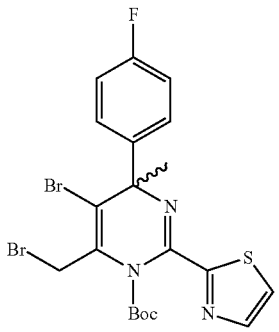 [SMILES: CC(C)(C)OC(=O)N1C(c2nccs2)=NC(C)(c2ccc(F)cc2)C(Br)=C1CBr]

Step 2-2a

To a solution of 1-ethynyl-4-fluorobenzene (21.500 g, 179 mmol) and allyl acetoacetate (25.4 g, 179 mmol) in xylene (170 ml) at rt was added indium (III) trifluoromethanesulfonate (2.012 g, 3.58 mmol). The mixture was heated at 120° C. for 3 h before being allowed to cool down and concentrated. The residue was diluted with DCM and hexanes (~2/1) and filtered. The filtrate was directly purified by flash column chromatography (silica, hexanes/EtOAc) to afford the desired compound as yellow oil (25.80 g, 55%). $^1$H NMR (400 MHz, CDCl$_3$) δ ppm 7.23-7.16 (m, 2H), 7.09-7.00 (m, 2H), 5.98-5.89 (m, 0.5H), 5.66-5.56 (m, 0.5H), 5.37-5.24 (m, 1H), 5.18-5.08 (m, 1H), 4.70 (dt, J=5.7, 1.4 Hz, 1H), 4.41 (dt, J=6.0, 1.3 Hz, 1H), 2.40 (s, 1.5H), 2.35 (s, 1.5H), 2.30 (s, 1.5H), 1.90 (s, 1.5H).

Step 2-2b

To a mixture of thiazole-2-carboximidamide hydrochloride (5.49 g, 33.6 mmol) and sodium bicarbonate (5.64 g, 67.1 mmol) in NMP (46 ml) at 120° C. was added a solution of the compound from Step 2-2a (8.80 g, 33.6 mmol) in NMP (20 ml). The mixture was heated at 120° C. under N$_2$ for 2.5 h before being allowed to cool down and diluted with MTBE and water. The organic layer was washed with water (*1), brine (*1), dried over Na$_2$SO$_4$ (s), filtered and concentrated. The residue was purified by flash column chromatography (silica, hexanes/EtOAc) to afford the desired compound as yellow oil (5.10 g, 41%). ESI MS m/z=372.13 [M+H]$^+$.

Step 2-2c

A solution of the compound from step 2-2b (5.10 g, 13.73 mmol), (Boc)$_2$O (5.74 ml, 24.72 mmol) and DMAP (3.35 g, 27.5 mmol) in DCM (60 ml) was stirred at rt for 3 h. The mixture was directly purified by flash column chromatography (silica, hexanes/EtOAc) to afford the desired compound as orange oil (5.50 g, 85%). ESI MS m/z=472.18 [M+H]$^+$.

Step 2-2d

To a mixture of the compound from step 2-2c (0.630 g, 1.336 mmol) and morpholine (0.122 ml, 1.403 mmol) in THF (8 ml) at rt was added Pd(PPh$_3$)$_4$ (0.077 g, 0.067 mmol). The mixture was stirred at rt under N$_2$ for 1.5 h before being concentrated. The residue was taken up with EtOAc and water. 1 N HCl aq (~1.5 ml) was added to get 2 clear layers. The organic layer was washed with brine (*1), dried over Na$_2$SO$_4$ (s), filtered and concentrated. The residue was purified by flash column chromatography (silica, hexanes/EtOAc) to afford the desired compound as yellow foam (0.576 g, 100%). ESI MS m/z=432.14 [M+H]$^+$.

Step 2-2e

To a solution of the compound from step 2-2d (0.290 g, 0.672 mmol) in DCM (6 ml) and heptane (6.00 ml) at rt was added NBS (0.251 g, 1.411 mmol). The resulting suspension was stirred at rt for 20 h before being diluted with DCM and saturated NaHCO$_3$ aq. The aqueous layer was extracted with DCM (*1). The combined organic layers were dried over Na$_2$SO$_4$ (s), filtered and concentrated. The residue was purified by flash column chromatography (silica, hexanes/EtOAc) to afford the title compound as colorless foam (0.344 g, 94%). ESI MS m/z=543.97, 545.97, 547.97 [M+H]$^+$.

Example 1

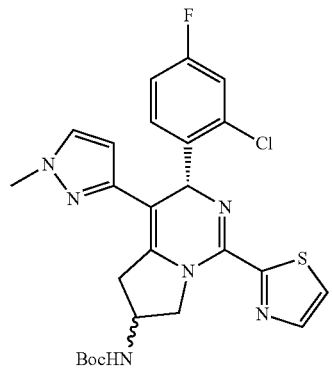 [SMILES: Cn1ccc(C2=C3CC(NC(=O)OC(C)(C)C)CN3C(c3nccs3)=N[C@H]2c2ccc(F)cc2Cl)n1]

Step 1a

To a solution of ethyl 2-nitroacetate (0.941 g, 7.07 mmol) in DMF (50 ml) at rt was added NaH (60% in mineral oil, 0.283 g, 7.07 mmol). The resulting solution was stirred at rt for 1 h before being cooled down to 0° C. Intermediate 1 (2.000 g, 3.54 mmol) was added at 0° C. The resulting solution was stirred at 0° C. for 2 h and then at rt overnight. It was quenched with saturated NH$_4$Cl aq and diluted with DCM and EtOAc. The organic layer was washed with water (*1), brine (*2), dried (Na$_2$SO$_4$) and concentrated. The residue was chromatographed (silica, hexanes/EtOAc) to afford the desired compound as yellow foam (0.903 g, 41%). ESI MS m/z=617.03, 619.03 [M+H]$^+$.

Step 1b

To a solution of the compound from step 1a (450 mg, 0.728 mmol) and 1-methyl-3-(tributylstannyl)-1H-pyrazole (351 mg, 0.947 mmol) in toluene (12 ml) at rt was added Pd(Ph$_3$P)$_4$ (126 mg, 0.109 mmol). The mixture was degassed 3 times before being heated at 135° C. using a microwave reactor for 45 min. The above reaction was repeated once. The reaction mixtures were combined and directly chromatographed (silica, hexanes/EtOAc) to afford the desired compound as yellow foam (525.0 mg, 58%). ESI MS m/z=619.16, 621.15 [M+H]$^+$.

Step 1c

A clear yellow-orange solution of the compound from step 1b (60 mg, 0.097 mmol) in DCM (2.0 ml) and TFA (1.0 ml) was stirred at rt for 1 h before being concentrated. The residue was co-evaporated with toluene (*2), then with DCM and some DIPEA. The residue was chromatographed (silica, hexanes/EtOAc) to afford the desired compound as yellow foam (42.0 mg, 84%). ESI MS m/z=519.10, 521.11 [M+H]$^+$.

Step 1d

Raney 2800 Ni (excess, slurry in Water) was washed with THF (*3). A solution of the compound from step 1c (42 mg, 0.081 mmol) in THF (2 ml) was added at rt, followed by (Boc)$_2$O (0.056 ml, 0.243 mmol). The resulting mixture was stirred at 50° C. with a H$_2$ balloon for 6 h. It was diluted with MeOH and filtered through a short pad of celite, washing with DCM/MeOH (1/1). The filtrate was concentrated. The residue was chromatographed (silica, hexanes/EtOAc) to afford the desired compound as yellow foam (21.0 mg, 44%). ESI MS m/z=589.18, 591.18 [M+H]$^+$.

Step 1e

To a solution of the compound from step 1d (21 mg, 0.036 mmol) in THF (2 ml) was added LiBH$_4$ (excess). The mixture was heated at 75° C. for 45 min before being allowed to cool down. 0.5 N HCl solution was added dropwise until no bubble was observed. The mixture was diluted with EtOAc and water. The organic layer was washed with brine, dried (Na$_2$SO$_4$) and concentrated. The residue was chromatographed (silica, hexanes/EtOAc) to afford the desired compound as yellow foam (11.8 mg, 60%). ESI MS m/z=547.17, 549.17 [M+H]$^+$.

Step 1f

To a solution of the compound from step 1e (11.8 mg, 0.022 mmol) in DCM (2 ml) at 0° C. was added Et$_3$N (6.01 μl, 0.043 mmol), followed by MsCl (2.52 μl, 0.032 mmol). The resulting mixture was stirred at 0° C. for 1 h before being diluted with DCM and water. The aqueous layer was extracted with DCM (*2). The combined organic layers were dried (Na$_2$SO$_4$) and concentrated. The residue was dried under vacuum to afford the desired compound as yellow foam (13.5 mg, 100%). ESI MS m/z=625.15, 627.15 [M+H]$^+$. MS showed ~50% of the product already cyclized.

Step 1 g

To a solution of the compound from step 1f (13.5 mg, 0.022 mmol) in DCM (2 ml) at rt was added Et$_3$N (6.02 μl, 0.043 mmol). The resulting mixture was stirred at rt for 1.5 h and then at 40° C. for 4 h. It was concentrated. The residue was chromatographed (silica, hexanes/EtOAc) to afford the title compound as yellow foam (10.0 mg, 88%). ESI MS m/z=529.16, 531.16 [M+H]$^+$.

Example 2

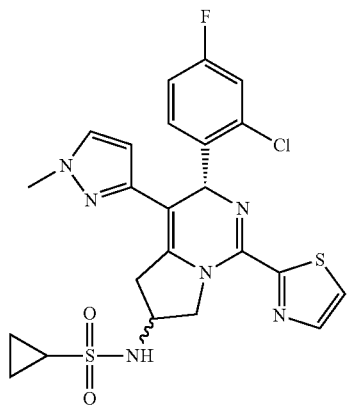 [SMILES: Cn1ccc(C2=C3CC(NS(=O)(=O)C4CC4)CN3C(c3nccs3)=N[C@H]2c2ccc(F)cc2Cl)n1]

Step 2a

To a solution of Example 1 (10.0 mg, 0.019 mmol) in DCM (2 ml) at rt was added 4N HCl in 1,4-dioxane (0.095 ml, 0.378 mmol). The resulting suspension was stirred at rt for 1 h. More 4 N HCl in 1,4-dioxane (0.095 ml, 0.378 mmol) was added. The suspension was stirred at rt for 1 h before being concentrated. The residue was co-evaporated with toluene and dried under vacuum to afford the desired compound as yellow foam (8.5 mg, 100%). ESI MS m/z=429.11, 431.11 [M+H]$^+$.

Step 2b

To a solution of the compound from step 2a (8.5 mg, 0.019 mmol) in pyridine (1 ml) at rt was added cyclopropanesulfonyl chloride (5.34 mg, 0.038 mmol). The resulting mixture was stirred at rt for 3 h and then heated at 30° C. overnight. DMAP (2.321 mg, 0.019 mmol) was added. The mixture was heated at 50° C. for 2 h before being allowed to cool down and quenched with water. It was concentrated. The residue was co-evaporated with toluene and chromatographed (silica, DCM/MeOH) to afford the title compound as yellow foam (4.7 mg, 44%). ESI MS m/z=533.10, 535.10 [M+H]$^+$.

$^1$H NMR showed it was a mixture of 2 diastereomers, dr ~3/2.

Example 3

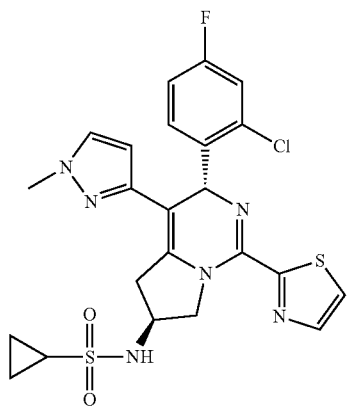 [SMILES: Cn1ccc(C2=C3C[C@H](NS(=O)(=O)C4CC4)CN3C(c3nccs3)=N[C@H]2c2ccc(F)cc2Cl)n1]

The title compound was obtained by chiral HPLC separation of Example 2 with Chiralpak OD-H column (eluting with 30% i-PrOH in hexanes). ESI MS m/z=533.10, 535.10 [M+H]+.

Alternative Route for the Preparation of Example 3

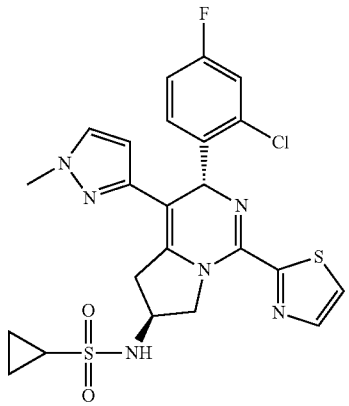 [SMILES: Cn1ccc(C2=C3C[C@H](NS(=O)(=O)C4CC4)CN3C(c3nccs3)=N[C@H]2c2ccc(F)cc2Cl)n1]

Step 3a

To a suspension of Intermediate 1 (3.00 g, 5.30 mmol) and ethyl 2-((diphenylmethylene)amino)acetate (1.985 g, 7.42 mmol) in toluene (54 ml) cooled at 0° C. was added O-Allyl-N-(9-anthracenylmethyl)cinchonidinium bromide (0.321 g, 0.530 mmol), followed by 50% KOH aq (17.68 ml, 265 mmol) dropwise. The mixture was vigorously stirred at 0° C. for 2 h before being diluted with saturated NaHCO$_3$ aq and MTBE. The organic layer was washed with saturated NaHCO$_3$ aq (*1), brine (*1), dried over Na$_2$SO$_4$ (s), filtered and concentrated. The residue was dried under vacuum to afford the desired compound as yellow foam (5.40 g), which was used directly for next step. ESI MS m/z=751.14, 753.14 [M+H]+.

Step 3b

A clear orange solution of the compound from step 3a (5.40 g, 5.30 mmol) in THF (30 ml), Water (30.00 ml) and AcOH (20.00 ml) was stirred at rt for 2.5 h before being concentrated. The residue was co-evaporated with DCM and some Et$_3$N (*1). It was purified by flash column chromatography (silica, hexanes/EtOAc) to afford the desired compound as yellow foam (2.540 g, 82% over 2 steps). ESI MS m/z=587.06, 589.06 [M+H]+. $^1$H NMR showed the dr was ~5/1.

Step 3c

To a clear yellow solution of the compound from step 3b (0.500 g, 0.851 mmol) in DCM (10 ml) at rt was added DMAP (0.208 g, 1.701 mmol), followed by Cbz-Cl (0.146 ml, 1.021 mmol). The solution was stirred at rt for 3 h before being quenched with saturated NaHCO$_3$ aq. and diluted with EtOAc and water. The organic layer was washed with brine (*1), dried over Na$_2$SO$_4$ (s), filtered and concentrated. The residue was purified by flash column chromatography (silica, hexanes/EtOAc) to afford the desired compound as yellow solid (0.284 g, 46%). ESI MS m/z=721.11, 723.11 [M+H]+.

Step 3d

To a solution of the compound from step 3c (0.284 g, 0.393 mmol) and 1-methyl-3-(tributylstannyl)-1H-pyrazole (0.190 g, 0.511 mmol) in toluene (8 ml) at rt was added Pd(Ph$_3$P)$_4$ (68.2 mg, 0.059 mmol). The mixture was degassed 3 times before being heated at 135° C. using a microwave reactor for 45 min. The mixture was directly purified by flash column chromatography (silica, hexanes/EtOAc) to afford the desired compound as yellow oil (0.240 g, 84%). ESI MS m/z=723.24, 725.24 [M+H]+.

Step 3e

A solution of the compound from step 3d (0.240 g, 0.332 mmol) in DCM (4 ml) and TFA (2.000 ml) was stirred at rt for 1 h. The mixture was concentrated. The residue was co-evaporated with toluene (*1), and then DCM with some Et$_3$N (*1). The residue was purified by flash column chromatography (silica, hexanes/EtOAc) to afford the desired compound as yellow solid (0.195 g, 94%). ESI MS m/z=623.18, 625.17 [M+H]+.

Step 3f

To a solution of the compound from step 3e (0.195 g, 0.313 mmol) in THF (6 ml) at rt was added LiBH$_4$ (1.0 M in THF, 0.939 ml, 0.939 mmol). The mixture was stirred at rt for 4.5 h. 1.0 N HCl solution was added dropwise until no bubble was observed. Excess tri-amine was added. The mixture was stirred at rt for 10 min before being diluted with EtOAc and saturated NH$_4$Cl aq. The organic layer was washed with brine (*1), dried over Na$_2$SO$_4$ (s), filtered and concentrated. The residue was purified by flash column chromatography (silica, hexanes/EtOAc) to afford the desired compound as yellow foam (0.165 g, 91%). ESI MS m/z=581.16, 583.16 [M+H]+.

Step 3g

To a yellow solution of the compound from step 3f (0.145 g, 0.250 mmol) in DCM (5 ml) cooled at 0° C. was added Et$_3$N (0.070 ml, 0.499 mmol), followed by a solution of MsCl (0.029 ml, 0.374 mmol) in DCM (0.1 ml). The resulting mixture was stirred at 0° C. for 1 h before being diluted with DCM and water. The aqueous layer was extracted with DCM (*2). The combined organic layers were dried over Na$_2$SO$_4$ (s), filtered and concentrated. The residue was taken up in DCM (5 ml). Et$_3$N (0.070 ml, 0.500 mmol) was added. The mixture was stirred at 40° C. for 6 h. The mixture was directly purified by flash column chromatography (silica, hexanes/EtOAc) to afford the desired compound as yellow foam (0.124 g, 88%). ESI MS m/z=563.15, 565.14 [M+H]+.

Step 3h

The compound from step 3g (2.420 g, 4.30 mmol) was treated with 30% HBr in acetic acid (15.56 ml, 86 mmol) at rt for 1 h. The mixture was freed of volatile by rotavapor. The residue oil was triturated with hexane/DCM (~2/1, *2). The residue oil was dissolved in MeOH and poured into excess 7 M NH$_3$ in MeOH at 0° C. The resulting clear solution was stirred at 0° C. for 15 min and then concentrated. The residue was partitioned between DCM and water. The aqueous layer was extracted with DCM (*2). The combined organic layers were dried over Na$_2$SO$_4$ (s), filtered and concentrated. The residue was purified by flash column chromatography (silica, hexanes/EtOAc) to afford the desired major diasteromers as yellow foam (1.410 g, 76%). ESI MS m/z=429.10, 431.09 [M+H]$^+$.

Step 3i

To a yellow solution of the compound from step 3h (26.1 mg, 0.061 mmol) in DCM (2 ml) at rt was added DMAP (14.87 mg, 0.122 mmol), followed by a solution of cyclopropanesulfonyl chloride (9.30 μl, 0.091 mmol) in DCM (0.1 ml). The solution was stirred at rt for 3 h before being quenched with excess i-PrOH at rt. The mixture was concentrated. The residue was purified by flash column chromatography (silica, hexanes/EtOAc) to afford the title compound as yellow foam (26.3 mg, 81%). ESI MS m/z=533.10, 535.10 [M+H]$^+$.

Example 4

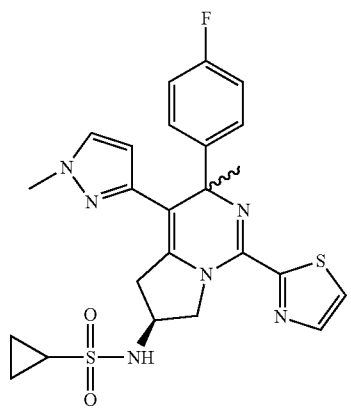 [SMILES: Cn1ccc(C2=C3C[C@H](NS(=O)(=O)C4CC4)CN3C(c3nccs3)=NC2(C)c2ccc(F)cc2)n1]

Step 4a

To a suspension of Intermediate 2 (0.945 g, 1.733 mmol) and ethyl 2-((diphenylmethylene)amino)acetate (0.927 g, 3.47 mmol) in toluene (17 ml) cooled at 0° C. was added O-Allyl-N-(9-anthracenylmethyl)cinchonidinium bromide (0.105 g, 0.173 mmol), followed by 50% KOH aq (5.78 ml, 87 mmol) dropwise. The mixture was vigorously stirred at 0° C. for 2 h before being diluted with saturated NaHCO$_3$ aq and MTBE. The organic layer was washed with saturated NaHCO$_3$ aq (*1), brine (*1), dried over Na$_2$SO$_4$ (s), filtered and concentrated. The residue was dried under vacuum to afford the desired compound as yellow foam (1.830 g), which was used directly for next step. ESI MS m/z=731.17, 733.17 [M+H]$^+$.

Step 4b

A clear orange solution of the compound from step 4a (1.268 g, 1.733 mmol) in THF (9 ml), Water (9.00 ml) and AcOH (6.00 ml) was stirred at rt for 4 h before being concentrated. The residue was taken up in DCM and saturated NaHCO$_3$ aq. The aqueous layer was extracted with DCM (*1). The combine organic layers were dried over Na$_2$SO$_4$ (s), filtered and concentrated. The residue was purified by flash column chromatography (silica, hexanes/EtOAc) to afford the desired compound as yellow foam (0.820 g, 83% over 2 steps). ESI MS m/z=567.11, 569.11 [M+H]$^+$.

Step 4c

To a clear yellow solution of the compound from step 4b (50.0 mg, 0.088 mmol) in DCM (0.6 ml) was added 4 M HCl in 1,4-dioxane (0.551 ml, 2.203 mmol) at rt. The resulting clear solution was stirred at rt for 0.5 h before being freed of volatiles. The residue was dissolved in DCM and washed with saturated NaHCO$_3$ aq. The aqueous layer was extracted with DCM (*1). The combine organic layers were dried over Na$_2$SO$_4$ (s), filtered and concentrated. The residue was dried under vacuum to afford the desired compound as yellow foam (40.8 mg), which was used directly for next step. ESI MS m/z=467.05, 469.05 [M+H]$^+$.

Step 4d

To a clear yellow solution of the compound from step 4c (40.8 mg, 0.087 mmol) in DCM (2 ml) at rt was added DMAP (21.33 mg, 0.175 mmol), followed by a solution of cyclopropanesulfonyl chloride (9.78 μl, 0.096 mmol) in DCM (0.1 ml) dropwise. The solution was stirred at rt for 3 h. Excess i-PrOH was added at rt to quench the reaction. After 5 min, the mixture was concentrated. The residue was purified by flash column chromatography (silica, hexanes/EtOAc) to afford the desired compound as yellow foam (40.6 mg, 81%). ESI MS m/z=571.05, 573.05 [M+H]$^+$.

Step 4e

To a solution of the compound from step 4d (40.6 mg, 0.071 mmol) in THF (1 ml) at rt was added a solution of LiBH$_4$ in THF (1.0 M, 0.213 ml, 0.213 mmol). The mixture was stirred at rt for 1.5 h. 0.5 N HCl solution was added dropwise until no bubble was observed. Excess tri-amine was added. The mixture was stirred at rt for 10 min before being diluted with EtOAc and water. The organic layer was washed with brine (*1), dried over Na$_2$SO$_4$ (s), filtered and concentrated. The residue was purified by flash column chromatography (silica, hexanes/EtOAc) to afford the desired compound as yellow foam (32.4 mg, 86%). ESI MS m/z=529.04, 531.04 [M+H]$^+$.

Step 4f

To a solution of the compound from step 4e (32.4 mg, 0.061 mmol) in 1,2-dichloroethane (2 ml) at rt was added triethylamine (0.026 ml, 0.184 mmol), followed by methanesulfonic anhydride (11.19 mg, 0.064 mmol). The solution was stirred at 55° C. for 2 h. More methanesulfonic anhydride (11.19 mg, 0.064 mmol) was added. The solution was stirred at 55° C. for 1.5 h before being allowed to cool down. Two drops of i-PrOH was added at rt. The mixture was directly purified by flash column chromatography (silica, hexanes/EtOAc) to afford the desired compound as yellow foam (27.4 mg, 88%). ESI MS m/z=511.03, 513.03 [M+H]$^+$.

Step 4 g

To a solution of the compound from step 4f (27.4 mg, 0.054 mmol) and 1-methyl-3-(tributylstannyl)-1H-pyrazole (25.9 mg, 0.070 mmol) in toluene (2 ml) at rt was added Pd(Ph₃P)₄ (9.29 mg, 8.04 μmol). The mixture was degassed 3 times before being heated at 135° C. using a microwave reactor for 45 min. The mixture was directly purified by flash column chromatography (silica, hexanes/EtOAc) to afford the title compound as yellow foam (19.2 mg, 70%). ESI MS m/z=513.15 [M+H]⁺.

Example 5

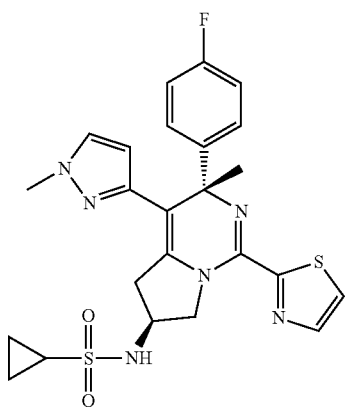 [SMILES: Cn1ccc(C2=C3C[C@H](NS(=O)(=O)C4CC4)CN3C(c3nccs3)=N[C@@]2(C)c2ccc(F)cc2)n1]

The title compound was obtained by chiral HPLC separation of Example 4 with Chiralpak OD-H column (eluting with 10% i-PrOH in hexanes). ESI MS m/z=513.15 [M+H]⁺.

Example 6

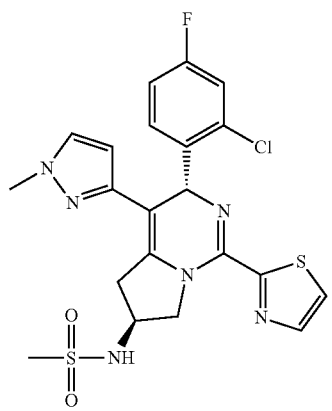 [SMILES: Cn1ccc(C2=C3C[C@H](NS(C)(=O)=O)CN3C(c3nccs3)=N[C@H]2c2ccc(F)cc2Cl)n1]

The title compound was prepared following similar procedure as step 3i. ESI MS m/z=507.08, 509.08 [M+H]⁺.

Example 7

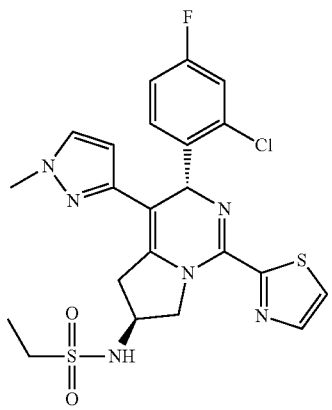 [SMILES: CCS(=O)(=O)N[C@H]1CC2=C(c3ccn(C)n3)[C@H](c3ccc(F)cc3Cl)N=C(c3nccs3)N2C1]

The title compound was prepared following similar procedure as step 3i. ESI MS m/z=521.10, 523.10 [M+H]⁺.

Example 8

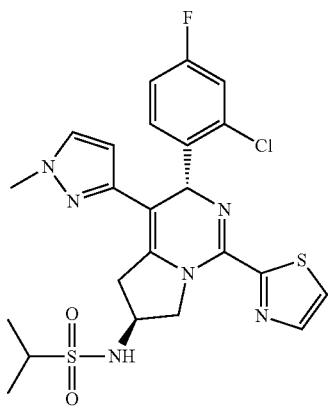 [SMILES: CC(C)S(=O)(=O)N[C@H]1CC2=C(c3ccn(C)n3)[C@H](c3ccc(F)cc3Cl)N=C(c3nccs3)N2C1]

The title compound was prepared following similar procedure as step 3i. ESI MS m/z=535.12, 537.12 [M+H]⁺.

Example 9

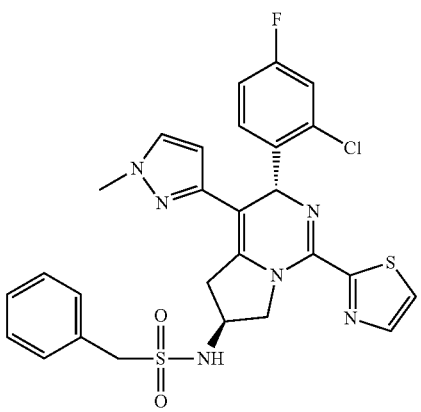 [SMILES: Cn1ccc(C2=C3C[C@H](NS(=O)(=O)Cc4ccccc4)CN3C(c3nccs3)=N[C@H]2c2ccc(F)cc2Cl)n1]

The title compound was prepared following similar procedure as step 3i. ESI MS m/z=583.12, 585.11 [M+H]⁺.

63

Example 10

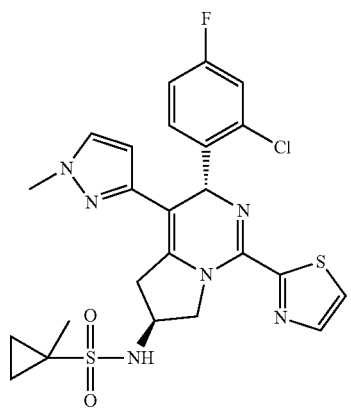 [SMILES: Cn1ccc(C2=C3C[C@H](NS(=O)(=O)C4(C)CC4)CN3C(c3nccs3)=N[C@H]2c2ccc(F)cc2Cl)n1]

The title compound was prepared following similar procedure as step 3i. ESI MS m/z=547.12, 549.11 [M+H]⁺.

Example 11

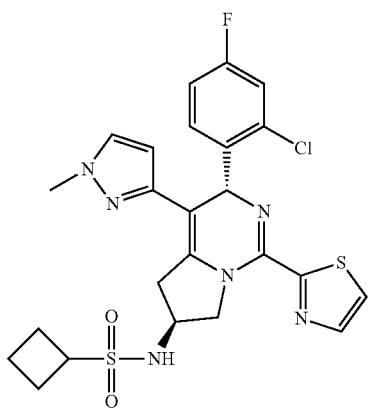 [SMILES: Cn1ccc(C2=C3C[C@H](NS(=O)(=O)C4CCC4)CN3C(c3nccs3)=N[C@H]2c2ccc(F)cc2Cl)n1]

The title compound was prepared following similar procedure as step 3i. ESI MS m/z=547.11, 549.11 [M+H]⁺.

Example 12

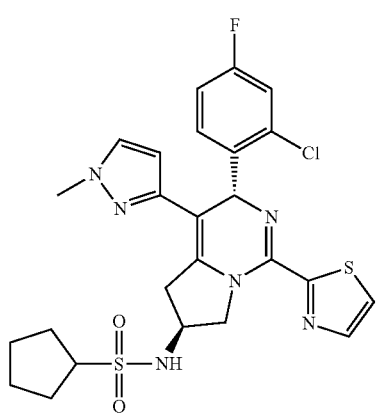 [SMILES: Cn1ccc(C2=C3C[C@H](NS(=O)(=O)C4CCCC4)CN3C(c3nccs3)=N[C@H]2c2ccc(F)cc2Cl)n1]

The title compound was prepared following similar procedure as step 3i. ESI MS m/z=579.10, 581.10 [M+H$_2$O+H]⁺.

64

Example 13

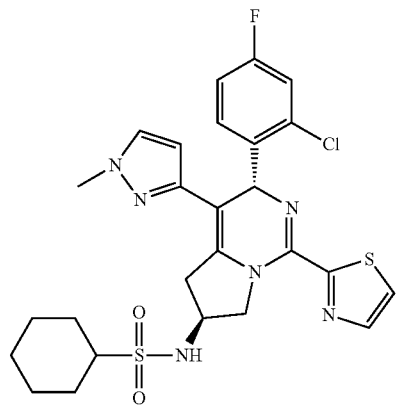 [SMILES: Cn1ccc(C2=C3C[C@H](NS(=O)(=O)C4CCCCC4)CN3C(c3nccs3)=N[C@H]2c2ccc(F)cc2Cl)n1]

The title compound was prepared following similar procedure as step 3i. ESI MS m/z=593.11, 595.11 [M+H$_2$O+H]⁺.

Example 14

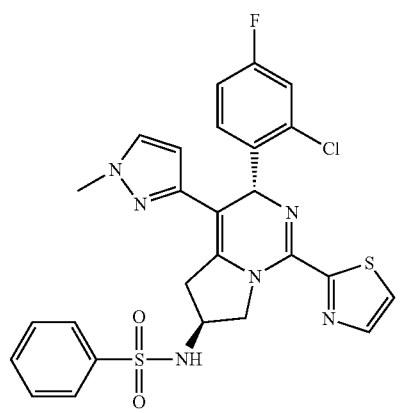 [SMILES: Cn1ccc(C2=C3C[C@H](NS(=O)(=O)c4ccccc4)CN3C(c3nccs3)=N[C@H]2c2ccc(F)cc2Cl)n1]

The title compound was prepared following similar procedure as step 3i. ESI MS m/z=569.10, 571.10 [M+H]⁺.

Example 15

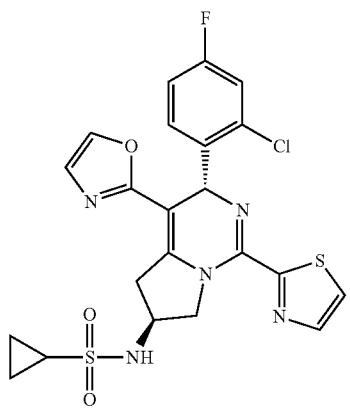 [SMILES: O=S(=O)(N[C@H]1CC2=C(c3ncco3)[C@H](c3ccc(F)cc3Cl)N=C(c3nccs3)N2C1)C1CC1]

The title compound was prepared following similar procedure as the alternative route for the preparation of Example 3. ESI MS m/z=520.07, 522.06 [M+H]⁺.

Example 16

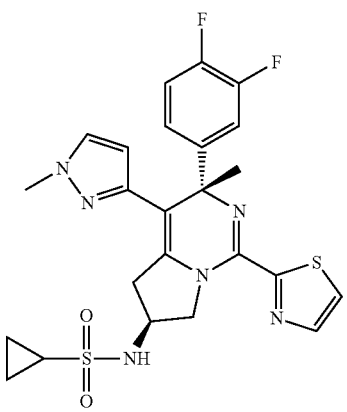 [SMILES: Cn1ccc(C2=C3C[C@H](NS(=O)(=O)C4CC4)CN3C(c3nccs3)=N[C@@]2(C)c2ccc(F)c(F)c2)n1]

The title compound was prepared following the similar procedure as that of Example 5. ESI MS m/z=531.14 [M+H]+.

Example 17

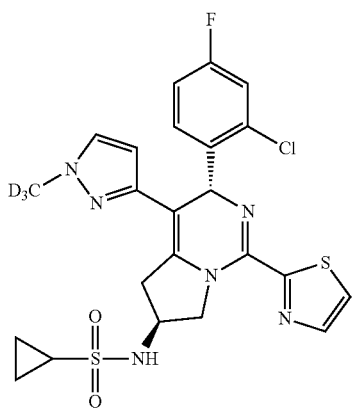 [SMILES: [2H]C([2H])([2H])n1ccc(C2=C3C[C@H](NS(=O)(=O)C4CC4)CN3C(c3nccs3)=N[C@H]2c2ccc(F)cc2Cl)n1]

The title compound was prepared following the similar procedure as that of Example 5. ESI MS m/z=536.12, 538.11 [M+H]+.

Example 18

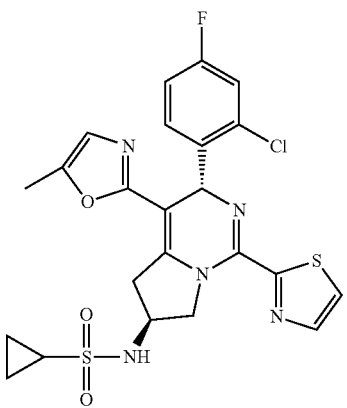 [SMILES: Cc1cnc(C2=C3C[C@H](NS(=O)(=O)C4CC4)CN3C(c3nccs3)=N[C@H]2c2ccc(F)cc2Cl)o1]

The title compound was prepared following the similar procedure as that of Example 5. ESI MS m/z=534.08, 536.08 [M+H]+.

Example 19

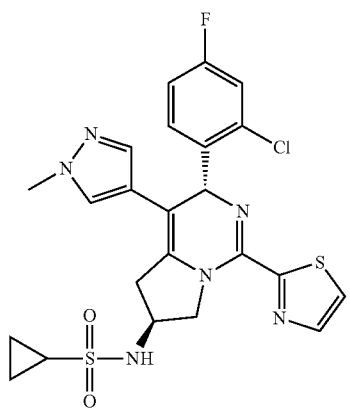 [SMILES: Cn1cc(C2=C3C[C@H](NS(=O)(=O)C4CC4)CN3C(c3nccs3)=N[C@H]2c2ccc(F)cc2Cl)cn1]

The title compound was prepared following the similar procedure as that of Example 5. ESI MS m/z=533.10, 535.10 [M+H]+.

Example 20

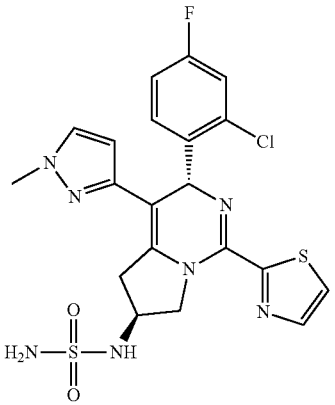 [SMILES: Cn1ccc(C2=C3C[C@H](NS(N)(=O)=O)CN3C(c3nccs3)=N[C@H]2c2ccc(F)cc2Cl)n1]

Step 20a. A solution of the compound from Step 3h (50.0 mg, 0.117 mmol) and sulfamide (33.6 mg, 0.350 mmol) in 1,4-dioxane (2 ml) was flushed with $N_2$ and then heated at 110° C. in a sealed tube for 5 h. The mixture was allowed to cool down and freed of volatiles with a stream of $N_2$. The residue was dissolved in DMSO (2 ml) and filtered. The filtrate was directly purified by HPLC (40-90% ACN in water) to afford the title compound as brown solid (42 mg, 72%). ESI MS m/z=508.07, 510.07 [M+H]+.

Example 21

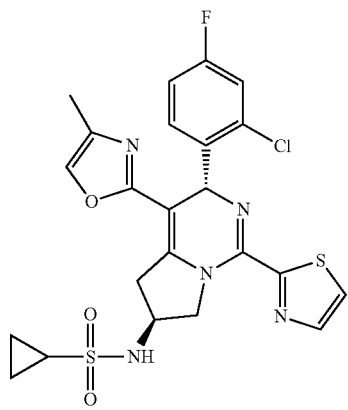 [SMILES: Cc1coc(C2=C3C[C@H](NS(=O)(=O)C4CC4)CN3C(c3nccs3)=N[C@H]2c2ccc(F)cc2Cl)n1]

The title compound was prepared following the similar procedure as that of Example 5. ESI MS m/z=534.08, 536.08 [M+H]+.

Example 22

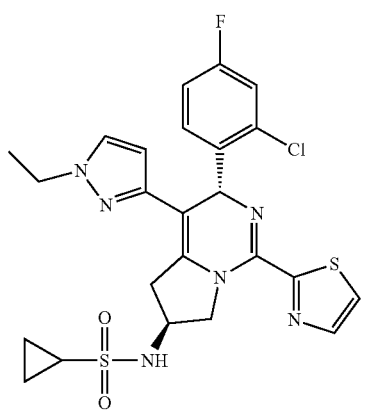 [SMILES: CCn1ccc(C2=C3C[C@H](NS(=O)(=O)C4CC4)CN3C(c3nccs3)=N[C@H]2c2ccc(F)cc2Cl)n1]

The title compound was prepared following the similar procedure as that of Example 5. ESI MS m/z=547.11, 549.11 [M+H]+.

Example 23

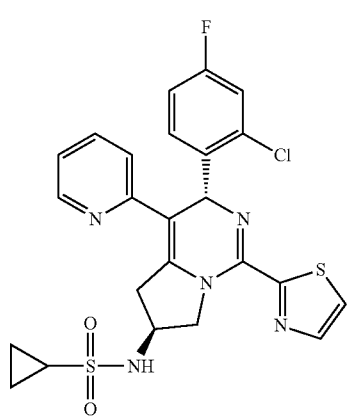 [SMILES: O=S(=O)(N[C@H]1CC2=C(c3ccccn3)[C@H](c3ccc(F)cc3Cl)N=C(c3nccs3)N2C1)C1CC1]

The title compound was prepared following the similar procedure as that of Example 5. ESI MS m/z=530.09, 532.09 [M+H]+.

Example 24

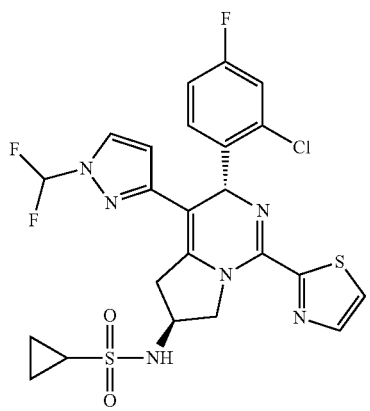 [SMILES: O=S(=O)(N[C@H]1CC2=C(c3ccn(C(F)F)n3)[C@H](c3ccc(F)cc3Cl)N=C(c3nccs3)N2C1)C1CC1]

The title compound was prepared following the similar procedure as that of Example 5. ESI MS m/z=569.08, 571.08 [M+H]+.

Example 25

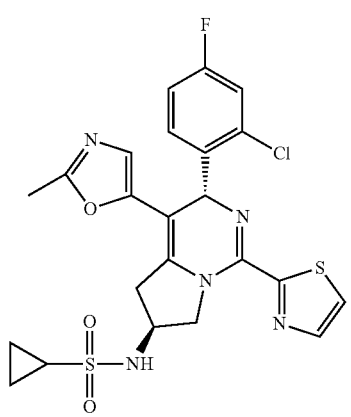 [SMILES: Cc1ncc(C2=C3C[C@H](NS(=O)(=O)C4CC4)CN3C(c3nccs3)=N[C@H]2c2ccc(F)cc2Cl)o1]

The title compound is prepared following the similar procedure as that of Example 5.

Example 26

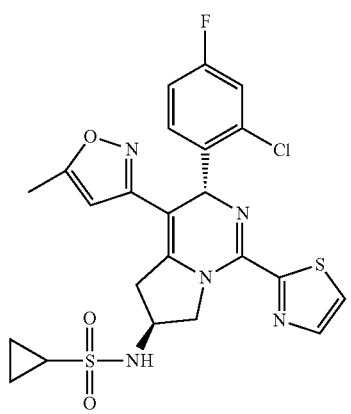 [SMILES: Cc1cc(C2=C3C[C@H](NS(=O)(=O)C4CC4)CN3C(c3nccs3)=N[C@H]2c2ccc(F)cc2Cl)no1]

The title compound is prepared following the similar procedure as that of Example 5.

Example 27

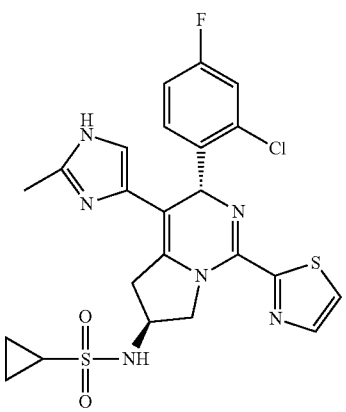 [SMILES: Cc1nc(C2=C3C[C@H](NS(=O)(=O)C4CC4)CN3C(c3nccs3)=N[C@H]2c2ccc(F)cc2Cl)c[nH]1]

The title compound is prepared following the similar procedure as that of Example 5.

Example 28

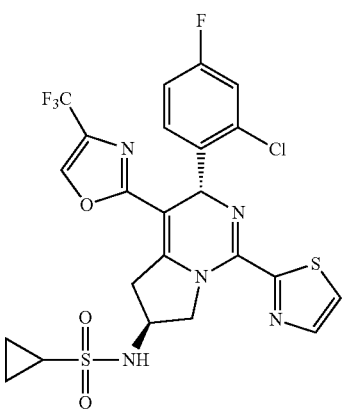 [SMILES: O=S(=O)(N[C@H]1CC2=C(c3nc(C(F)(F)F)co3)[C@H](c3ccc(F)cc3Cl)N=C(c3nccs3)N2C1)C1CC1]

The title compound is prepared following the similar procedure as that of Example 5.

Biological Activity

Methods: HepAD38 cells are maintained as previously reported (Ladner et al, *Antimicrob. Agents Chemother.* 1997, 4, 1715). Briefly, cells are passaged upon attaining confluency in DMEM/F12 media in the presence of 10% FBS, Penn/Strep, 250 μg/mL G418, and 1 μg/ml tetracycline. Novel compounds are screened by first washing cells three times with PBS to remove tetracycline, and plating in 96 well plates at 35,000 cells/well. Compounds dissolved in DMSO are then diluted 1:200 into wells containing cells. Five days after compound addition, material is harvested for analysis. For an extended 8 day analysis, cells are plated and treated as described above, but media and compound are refreshed on d2 and d5 post initial treatment.

On harvest day, virion DNA is obtained by lysing with Sidestep Lysis and Stabilization Buffer and then quantified via quantitative real time PCR. Commercially available ELISA kits are used to quantitate the viral proteins HBsAg (Alpco) or HbeAg (US Biological) by following the manufacturer's recommended protocol after diluting samples to match the linear range of their respective assays. Irrespective of readout, compound concentrations that reduce viral product accumulation in the cell lysates or supernatants by 50% relative to no drug controls ($EC_{50}$) are reported; $EC_{50}$ ranges are as follows: A<0.1 μM; B 0.1-1 μM; C>1 μM.

Compound toxicity is evaluated by seeding cells at 15,000 cells/well and treating with compound as described above. Three days after compound addition, cells are treated with ATPLite reagent and compound concentrations that reduce total ATP levels in wells by 50% relative to no drug controls ($CC_{50}$) are reported; $CC_{50}$ ranges are as follows: A>25 μM; B 10-25 μM; C<10 μM.

TABLE 1

Summary of Activities

| Compd. Number | HepAD38 $EC_{50}$ (μM) | HepG2 $CC_{50}$ (μM) |
|---|---|---|
| 1 | A | C |
| 2 | A | A |
| 3 | A | |
| 4 | A | |
| 5 | A | |
| 6 | A | |
| 7 | A | |
| 8 | A | |
| 9 | A | |
| 10 | A | |
| 11 | A | |
| 12 | A | |
| 13 | A | |
| 14 | A | |
| 15 | A | |
| 16 | A | |
| 17 | A | A |
| 18 | A | A |
| 19 | A | |
| 20 | A | A |
| 21 | A | |
| 22 | A | >6 |
| 23 | B | |

While this invention has been particularly shown and described with references to preferred embodiments thereof, it will be understood by those skilled in the art that various changes in form and details may be made therein without departing from the scope of the invention encompassed by the appended claims.

What is claimed:
1. A compound represented by Formula (I):

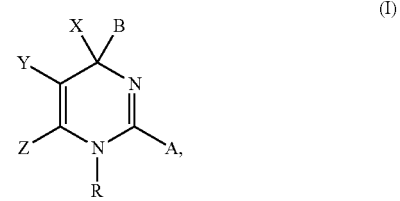

or a pharmaceutically acceptable salt thereof, wherein:
A is optionally substituted monocyclic heteroaryl;
B is hydrogen or methyl;
X is optionally substituted phenyl;
Y is optionally substituted phenyl or optionally substituted monocyclic heteroaryl; and
R and Z are taken together with the atoms to which they are attached to form an optionally substituted 4- to 12-membered heterocyclic.

2. The compound of claim 1, wherein A is selected from the following by removal of one hydrogen atom:

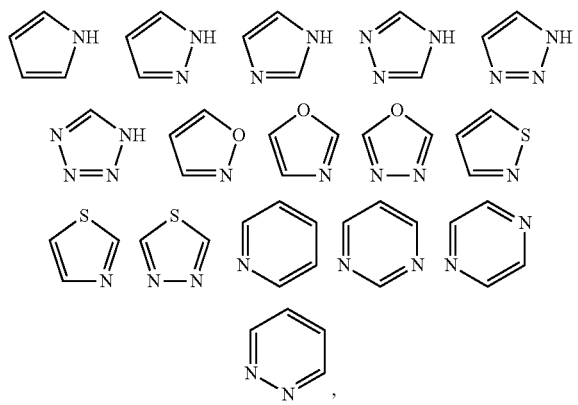

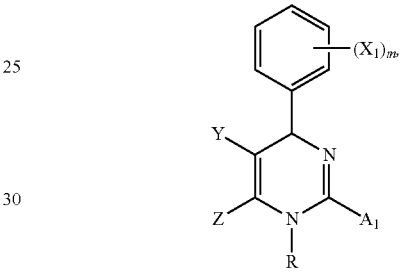

wherein each of the above shown groups is optionally substituted.

3. The compound of claim 1, wherein Y is selected from the following:

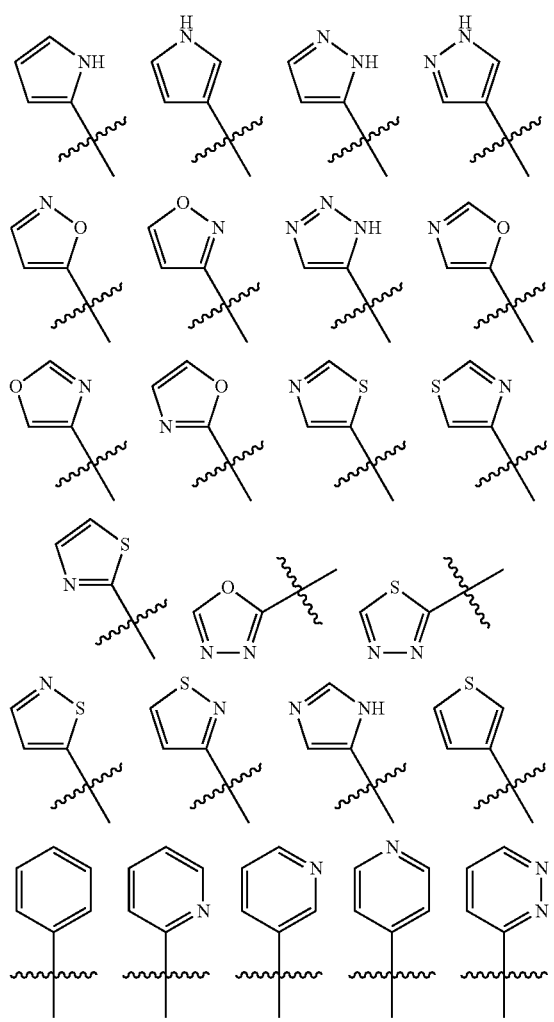

wherein each of the above shown groups is optionally substituted.

4. The compound of claim 1, represented by Formula (IIa-1), or a pharmaceutically acceptable salt thereof,

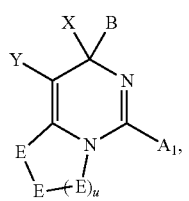

IIa-1 wherein $A_1$ is a 5- or 6-membered heteroaryl group containing 1 to 4 heteroatoms selected from O, N, and S; each $X_1$ is independently optionally substituted methyl, halo, CN, $OR_{11}$, or $NR_{11}R_{12}$; m is 0, 1, 2, 3, 4 or 5; $R_{11}$ and $R_{12}$ are each selected from the group consisting of hydrogen, optionally substituted $C_1$-$C_8$ alkyl, optionally substituted —$C_2$-$C_8$ alkenyl, optionally substituted —$C_2$-$C_8$ alkynyl, and optionally substituted —$C_3$-$C_8$ cycloalkyl; and R, Y and Z are as defined in claim 1.

5. The compound of claim 1, represented by Formula (IIIa), or a pharmaceutically acceptable salt thereof, IIIa wherein $A_1$ is a 5- or 6-membered heteroaryl group containing 1 to 4 heteroatoms selected from O, N, and S; E at each occurrence is the same or different and independently selected from —$CR_{15}R_{16}$—, —C(O)—, —O—, —$NR_{16}$—, —S—, and —$S(O)_2$—; u is 0, 1, 2, or 3; $R_{15}$ is hydrogen, halo, CN, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; $R_{16}$ is hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; alternatively, two vicinal E groups are taken together to form an optionally substituted carbon-carbon double bond or an optionally substituted fused ring and X, B, and Y are as defined in claim 1.

6. The compound of claim 5, represented by Formula (IIIa) or (IIIb), or a pharmaceutically acceptable salt thereof, wherein

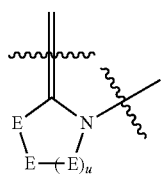

is selected from the groups below:

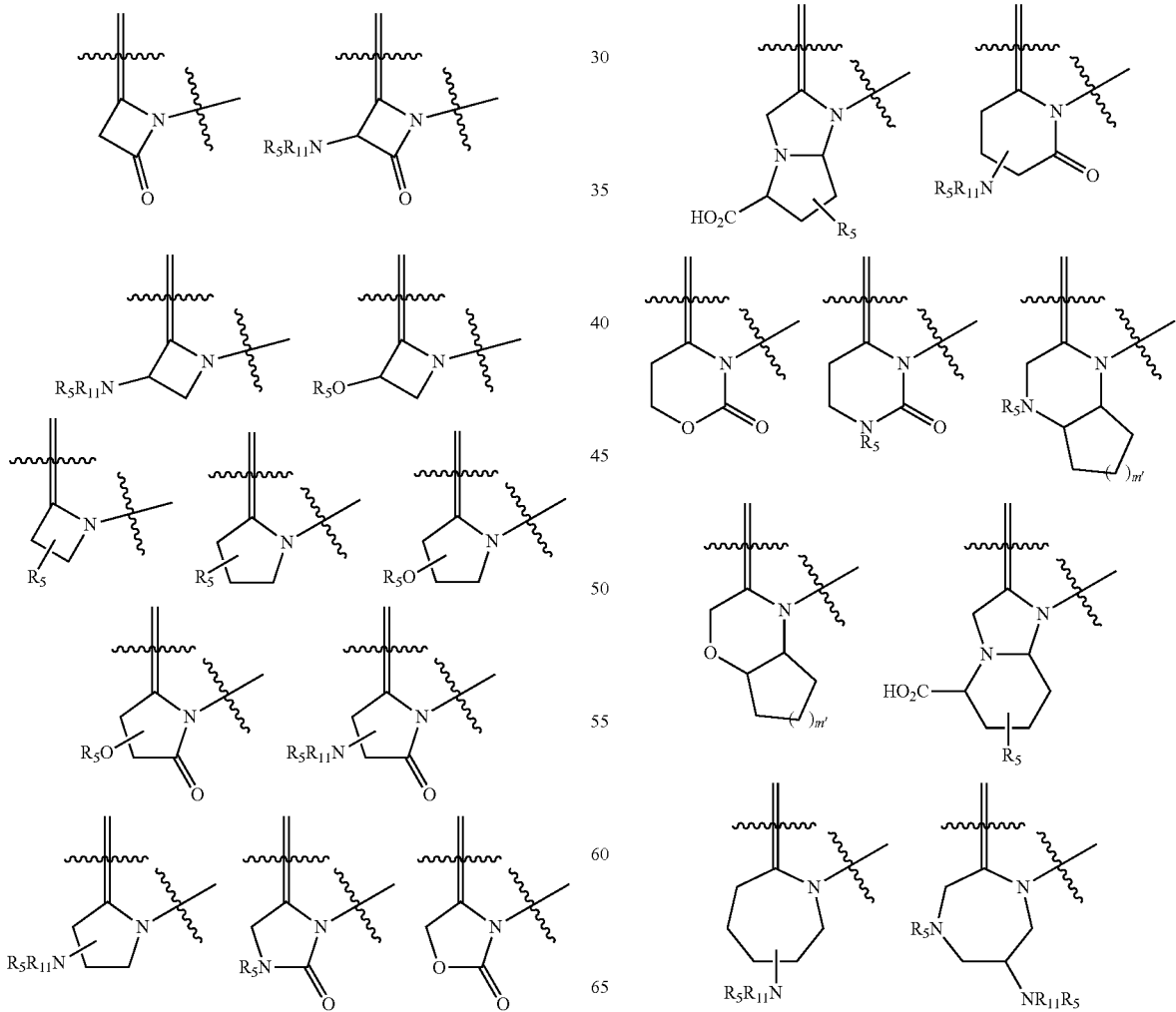

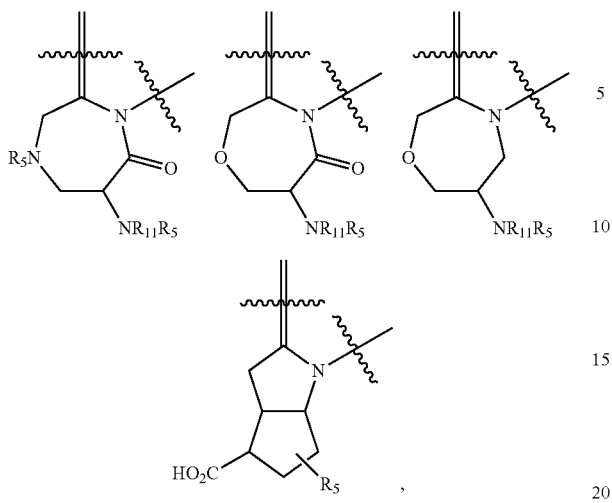

wherein each of the above shown groups is optionally substituted; each $R_3$ is independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, —CN, —$OR_{11}$, and —$NR_{11}R_{12}$; $R_5$ is selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl, optionally substituted heteroaryl, —$C(O)R_{11}$, —$C(O)OR_{11}$, —$C(O)NR_{11}R_{12}$, —$S(O)_2R_{11}$, and —$S(O)_2NR_{11}R_{12}$; $R_{11}$ and $R_{12}$ at each occurrence are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; and m' is 1, 2, or 3.

7. The compound of claim 1, selected from the compounds set forth below or a pharmaceutically acceptable salt thereof:

| Compound | Structure |
|----------|-----------|
| 1 | 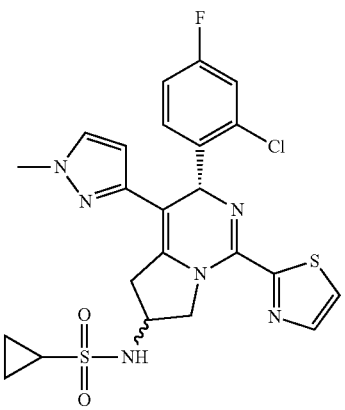 [SMILES: Cn1ccc(C2=C3CC(NS(=O)(=O)C4CC4)CN3C(c3nccs3)=N[C@H]2c2ccc(F)cc2Cl)n1] |
| 2 | 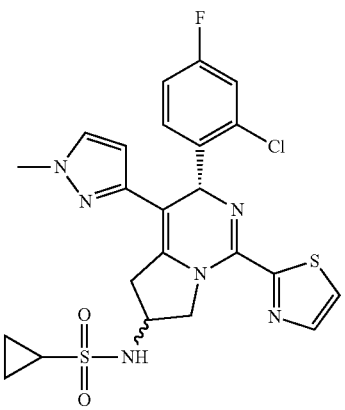 [SMILES: Cn1ccc(C2=C3CC(NS(=O)(=O)C4CC4)CN3C(c3nccs3)=N[C@H]2c2ccc(F)cc2Cl)n1] |
| 3 | 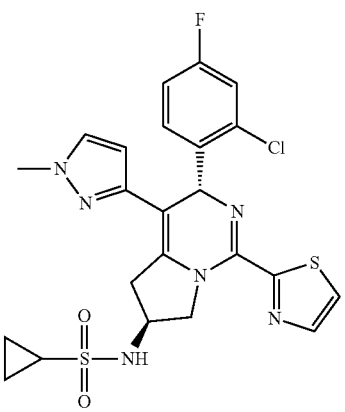 [SMILES: Cn1ccc(C2=C3C[C@H](NS(=O)(=O)C4CC4)CN3C(c3nccs3)=N[C@H]2c2ccc(F)cc2Cl)n1] |
| 4 | 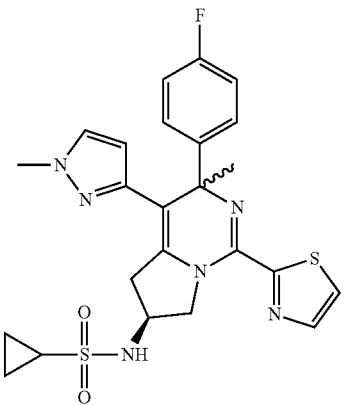 [SMILES: Cn1ccc(C2=C3C[C@H](NS(=O)(=O)C4CC4)CN3C(c3nccs3)=NC2(C)c2ccc(F)cc2)n1] |

| Compound | Structure |
|---|---|
| 5 | 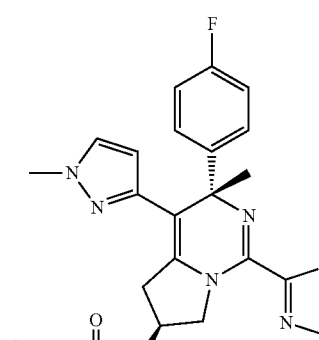 |
| 6 | 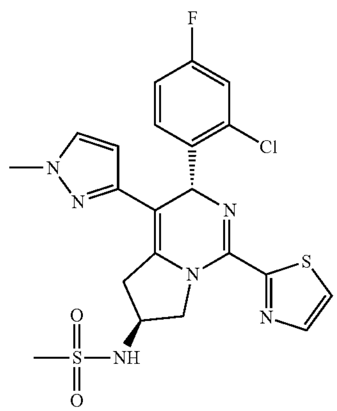 [SMILES: Cn1ccc(C2=C3C[C@H](NS(C)(=O)=O)CN3C(c3nccs3)=N[C@H]2c2ccc(F)cc2Cl)n1] |
| 7 | 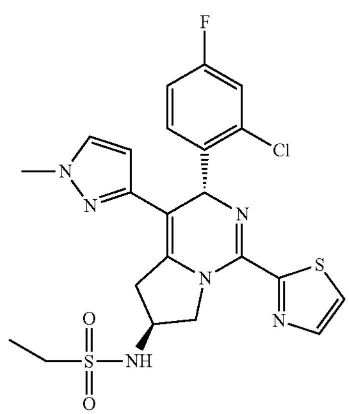 [SMILES: CCS(=O)(=O)N[C@H]1CC2=C(c3ccn(C)n3)[C@H](c3ccc(F)cc3Cl)N=C(c3nccs3)N2C1] |
| 8 | 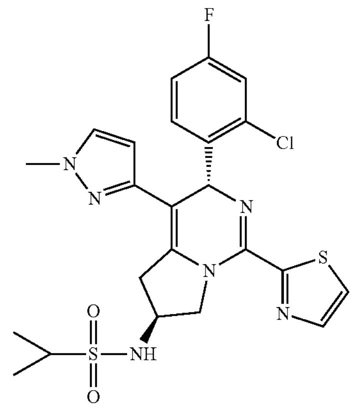 [SMILES: CC(C)S(=O)(=O)N[C@H]1CC2=C(c3ccn(C)n3)[C@H](c3ccc(F)cc3Cl)N=C(c3nccs3)N2C1] |
| 9 | 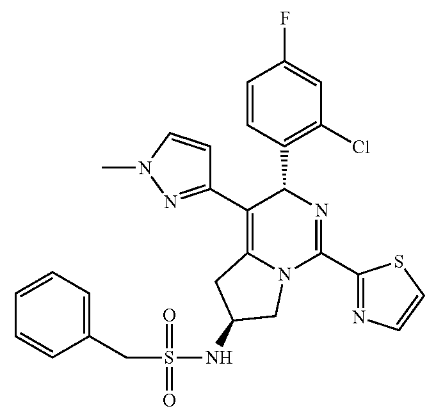 [SMILES: Cn1ccc(C2=C3C[C@H](NS(=O)(=O)Cc4ccccc4)CN3C(c3nccs3)=N[C@H]2c2ccc(F)cc2Cl)n1] |
| 10 | 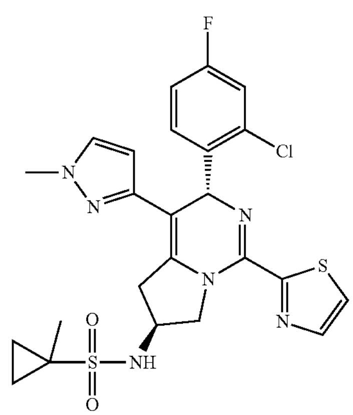 [SMILES: Cn1ccc(C2=C3C[C@H](NS(=O)(=O)C4(C)CC4)CN3C(c3nccs3)=N[C@H]2c2ccc(F)cc2Cl)n1] |

| Compound | Structure |
|---|---|
| 11 | *(structure: 4-fluoro-2-chlorophenyl and 1-methylpyrazole substituted pyrrolopyrimidine with thiazole and cyclobutanesulfonamide)* |
| 12 | *(structure: 4-fluoro-2-chlorophenyl and 1-methylpyrazole substituted pyrrolopyrimidine with thiazole and cyclopentanesulfonamide)* |
| 13 | *(structure: 4-fluoro-2-chlorophenyl and 1-methylpyrazole substituted pyrrolopyrimidine with thiazole and cyclohexanesulfonamide)* |
| 14 | *(structure: 4-fluoro-2-chlorophenyl and 1-methylpyrazole substituted pyrrolopyrimidine with thiazole and phenylsulfonamide)* |
| 15 | *(structure: 4-fluoro-2-chlorophenyl and oxazole substituted pyrrolopyrimidine with thiazole and cyclopropanesulfonamide)* |
| 16 | *(structure: 3,4-difluorophenyl with methyl, 1-methylpyrazole substituted pyrrolopyrimidine with thiazole and cyclopropanesulfonamide)* |

-continued

| Compound | Structure |
|---|---|
| 17 | (chemical structure: 4-fluoro-2-chlorophenyl; N-CD3 pyrazole; thiazole; cyclopropanesulfonamide) |
| 18 | (chemical structure: 4-fluoro-2-chlorophenyl; 5-methyloxazole; thiazole; cyclopropanesulfonamide) |
| 19 | (chemical structure: 4-fluoro-2-chlorophenyl; N-methylpyrazol-4-yl; thiazole; cyclopropanesulfonamide) |

-continued

| Compound | Structure |
|---|---|
| 20 | (chemical structure: 4-fluoro-2-chlorophenyl; N-methylpyrazole; thiazole; sulfamide) |
| 21 | (chemical structure: 4-fluoro-2-chlorophenyl; 4-methyloxazole; thiazole; cyclopropanesulfonamide) |
| 22 | (chemical structure: 4-fluoro-2-chlorophenyl; N-ethylpyrazole; thiazole; cyclopropanesulfonamide) |

| Compound | Structure |
|---|---|
| 23 | (structure) |
| 24 | (structure) |
| 25 | (structure) |
| 26 | (structure) |
| 27 | (structure) |
| 28 | (structure) |

8. A pharmaceutical composition, comprising a compound according to claim 1 or a pharmaceutically acceptable salt thereof, in combination with a pharmaceutically acceptable carrier or excipient.

* * * * *

UNITED STATES PATENT AND TRADEMARK OFFICE
CERTIFICATE OF CORRECTION

PATENT NO. : 10,189,846 B2
APPLICATION NO. : 15/617445
DATED : January 29, 2019
INVENTOR(S) : Yao-Ling Qiu et al.

Page 1 of 1

It is certified that error appears in the above-identified patent and that said Letters Patent is hereby corrected as shown below:

In the Claims

<u>At Column 72</u>
In Claim 5, at Line 63, after CN, add -- -$NR_{11}R_{12}$, --.

Signed and Sealed this
Seventh Day of May, 2019

Andrei Iancu
*Director of the United States Patent and Trademark Office*